United States Patent
Jarrett et al.

(10) Patent No.: US 10,905,765 B2
(45) Date of Patent: Feb. 2, 2021

(54) MEDICAL ORGANOGEL PROCESSES AND COMPOSITIONS

(71) Applicant: Incept, LLC, Lexington, MA (US)

(72) Inventors: Peter Jarrett, Lexington, MA (US); Rami El-Hayek, Norwood, MA (US); Amarpreet S. Sawhney, Lexington, MA (US)

(73) Assignee: Incept, LLC, Lexington, MA (US)

( * ) Notice: Subject to any disclaimer, the term of this patent is extended or adjusted under 35 U.S.C. 154(b) by 485 days.

(21) Appl. No.: 14/926,707

(22) Filed: Oct. 29, 2015

(65) Prior Publication Data

US 2016/0045602 A1 Feb. 18, 2016

Related U.S. Application Data

(62) Division of application No. 13/705,808, filed on Dec. 5, 2012, now Pat. No. 9,205,150.

(60) Provisional application No. 61/566,768, filed on Dec. 5, 2011.

(51) Int. Cl.
| | | |
|---|---|---|
| A61K 47/34 | (2017.01) | |
| A61K 9/06 | (2006.01) | |
| A61K 38/38 | (2006.01) | |
| C07K 16/00 | (2006.01) | |
| A61K 9/00 | (2006.01) | |

(52) U.S. Cl.
CPC ........... *A61K 47/34* (2013.01); *A61K 9/06* (2013.01); *A61K 38/38* (2013.01); *C07K 16/00* (2013.01); *A61K 9/0051* (2013.01)

(58) Field of Classification Search
None
See application file for complete search history.

(56) References Cited

U.S. PATENT DOCUMENTS

| | | |
|---|---|---|
| 3,161,602 A | 12/1964 | Herbig et al. |
| 3,423,489 A | 1/1969 | Arens et al. |
| 3,640,741 A | 2/1972 | Etes |
| 3,779,942 A | 12/1973 | Bolles |
| 3,991,766 A | 11/1976 | Schmitt et al. |
| 4,002,173 A | 1/1977 | Manning et al. |
| 4,107,288 A | 8/1978 | Oppenheim et al. |
| 4,193,813 A | 3/1980 | Chvapil |
| 4,268,495 A | 5/1981 | Muxfeldt et al. |
| 4,424,311 A | 1/1984 | Nagaoka et al. |
| 4,456,711 A | 6/1984 | Pietsch et al. |
| 4,472,542 A | 9/1984 | Nambu |
| 4,530,840 A | 7/1985 | Tice et al. |
| 4,631,188 A | 12/1986 | Stoy et al. |
| 4,664,857 A | 5/1987 | Nambu |
| 4,703,108 A | 10/1987 | Silver et al. |
| 4,734,097 A | 3/1988 | Tanabe et al. |
| 4,741,872 A | 5/1988 | DeLuca et al. |
| 4,760,131 A | 7/1988 | Sundsmo et al. |
| 4,837,381 A | 6/1989 | Steber et al. |
| 4,839,345 A | 6/1989 | Dio et al. |
| 4,853,224 A | 8/1989 | Wong |
| 4,925,677 A | 5/1990 | Feijen |
| 4,938,763 A | 7/1990 | Dunn et al. |
| 4,948,572 A | 8/1990 | Cole et al. |
| 4,948,575 A | 8/1990 | Cole et al. |
| 4,952,581 A | 8/1990 | Bito et al. |
| 4,970,298 A | 11/1990 | Silver et al. |
| 5,024,742 A | 6/1991 | Nesbum et al. |
| 5,041,292 A | 8/1991 | Feijen |
| 5,100,992 A | 5/1992 | Cohn et al. |
| 5,143,662 A | 9/1992 | Chesterfield et al. |
| 5,147,647 A | 9/1992 | Darougar et al. |
| 5,158,152 A | 10/1992 | Nemoto et al. |
| 5,160,745 A | 11/1992 | DeLuca et al. |
| 5,162,430 A | 11/1992 | Rhee et al. |
| 5,185,152 A | 2/1993 | Peyman |
| 5,192,743 A | 3/1993 | Hsu et al. |
| 5,198,220 A | 3/1993 | Damani |
| 5,227,372 A | 7/1993 | Folkman |
| 5,232,984 A | 8/1993 | Hubbell et al. |
| 5,266,325 A | 11/1993 | Kuzman et al. |
| 5,278,202 A | 1/1994 | Dunn et al. |
| 5,296,504 A | 3/1994 | Stjernchantz et al. |
| 5,304,595 A | 4/1994 | Rhee et al. |
| 5,306,500 A | 4/1994 | Rhee et al. |
| 5,322,691 A | 6/1994 | Darougar et al. |
| 5,324,775 A | 6/1994 | Rhee et al. |

(Continued)

FOREIGN PATENT DOCUMENTS

| | | |
|---|---|---|
| WO | 94/01136 | 1/1994 |
| WO | 9722371 | 6/1997 |

(Continued)

OTHER PUBLICATIONS

Jain et al. Cyclosporin A loaded Plga nanoparticle: preparation, optimization, in-vitro characterization and stability studies. Jun. 2010 Curr. Nanosci. 6: 10 p. (Year: 2010).*
Bos et al., "Controlled release of pharmaceutical proteins from hydrogels", Business Briefing Pharmatech, pp. 1-5 (2002).
Dong et al., "Dextran Permeation Through Poly (N-Isopropylacrylamide) Hydrogels," J. Biomater. Sci., Polymer vol. 5(5):473-484 (1994).
Galeska et al., "Controlled Release of Dexamethasone from PLGA Microspheres Embedded Within Polyacid-Containing PVA Hydrogels", AAPS Journal, vol. 7(1):E231-E240 (Sep. 2, 2005).
Sander et al., "Crosslinked Poly(alkylene Oxides) for the Preparation of Controlled Release Micromatrices", Journal of Controlled Release, 5:271-283 (1988).

(Continued)

*Primary Examiner* — Jennifer Lamberski
(74) *Attorney, Agent, or Firm* — Peter S. Dardi; Diane E. Bennett

(57) ABSTRACT

Serial-solvent biomaterials are described. Embodiments include materials made in an organic solvent that are stripped of the solvent and used in a patient, where they imbibe water and form a hydrogel. These materials are useful for, among other things, delivering therapeutic agents, tissue augmentation, and radiological marking.

16 Claims, 8 Drawing Sheets

(56) References Cited

U.S. PATENT DOCUMENTS

| | | |
|---|---|---|
| 5,328,955 A | 7/1994 | Rhee et al. |
| 5,330,768 A | 7/1994 | Park et al. |
| 5,350,399 A | 9/1994 | Erlebacher et al. |
| 5,376,375 A | 12/1994 | Rhee et al. |
| 5,380,536 A | 1/1995 | Hubbell et al. |
| 5,395,618 A | 3/1995 | Darougar et al. |
| 5,409,703 A | 4/1995 | McAnalley et al. |
| 5,410,016 A | 4/1995 | Hubbell et al. |
| 5,413,791 A | 5/1995 | Rhee et al. |
| 5,426,148 A | 6/1995 | Tucker |
| 5,446,090 A | 8/1995 | Harris |
| 5,446,091 A | 8/1995 | Rhee et al. |
| 5,462,990 A | 10/1995 | Hubbell et al. |
| 5,470,911 A | 11/1995 | Rhee et al. |
| 5,475,052 A | 12/1995 | Rhee et al. |
| 5,480,914 A | 1/1996 | Meadows |
| 5,482,927 A | 1/1996 | Maniar et al. |
| 5,499,994 A | 3/1996 | Tihon et al. |
| 5,510,418 A | 4/1996 | Rhee et al. |
| 5,514,379 A | 5/1996 | Weissleder et al. |
| 5,514,380 A | 5/1996 | Song et al. |
| 5,527,856 A | 6/1996 | Rhee et al. |
| 5,529,914 A | 6/1996 | Hubbell et al. |
| 5,530,528 A | 6/1996 | Houki et al. |
| 5,543,441 A | 8/1996 | Rhee et al. |
| 5,550,187 A | 8/1996 | Rhee et al. |
| 5,550,188 A | 8/1996 | Rhee et al. |
| 5,565,519 A | 10/1996 | Rhee et al. |
| 5,573,934 A | 11/1996 | Hubbell et al. |
| 5,578,638 A | 11/1996 | Brazzell et al. |
| 5,589,194 A | 12/1996 | Tsuei et al. |
| 5,599,552 A | 2/1997 | Dunn et al. |
| 5,612,052 A | 3/1997 | Shalaby |
| 5,614,587 A | 3/1997 | Rhee et al. |
| 5,618,563 A | 4/1997 | Berde et al. |
| 5,629,008 A | 5/1997 | Lee |
| 5,643,464 A | 7/1997 | Rhee et al. |
| 5,650,173 A | 7/1997 | Ramstack et al. |
| 5,660,849 A | 8/1997 | Polson et al. |
| 5,662,712 A | 9/1997 | Pathak et al. |
| 5,665,840 A | 9/1997 | Pohlmann et al. |
| 5,681,576 A | 10/1997 | Henry |
| 5,705,194 A | 1/1998 | Wong et al. |
| 5,707,643 A | 1/1998 | Ogura et al. |
| 5,714,159 A | 2/1998 | Shalaby |
| 5,718,916 A | 2/1998 | Scherr |
| 5,723,269 A | 3/1998 | Akagi et al. |
| 5,741,292 A | 4/1998 | Mendius |
| 5,744,545 A | 4/1998 | Rhee et al. |
| 5,752,974 A | 5/1998 | Rhee et al. |
| 5,759,583 A | 6/1998 | Iwamoto et al. |
| 5,770,229 A | 6/1998 | Tahuhar et al. |
| 5,773,019 A | 6/1998 | Ashton et al. |
| 5,773,025 A | 6/1998 | Baichwal |
| 5,776,493 A | 7/1998 | Barclay et al. |
| 5,786,421 A | 7/1998 | Rhee et al. |
| 5,800,373 A | 9/1998 | Mealanson et al. |
| 5,800,541 A | 9/1998 | Rhee et al. |
| 5,800,841 A | 9/1998 | Rhee et al. |
| 5,807,581 A | 9/1998 | Rosenblatt et al. |
| 5,814,621 A | 9/1998 | Kanaya et al. |
| 5,820,882 A | 10/1998 | Hubbell et al. |
| 5,823,198 A | 10/1998 | Jones et al. |
| 5,824,037 A | 10/1998 | Fogarty et al. |
| 5,830,171 A | 11/1998 | Wallace |
| 5,837,226 A | 11/1998 | Jungherr et al. |
| 5,843,743 A | 12/1998 | Hubbell et al. |
| 5,844,016 A | 12/1998 | Sawhney et al. |
| 5,844,023 A | 12/1998 | Tomka |
| 5,849,035 A | 12/1998 | Pathak et al. |
| 5,849,412 A | 12/1998 | Bromberg et al. |
| 5,849,839 A | 12/1998 | Hubbell et al. |
| 5,863,984 A | 1/1999 | Doilon et al. |
| 5,869,096 A | 2/1999 | Barclay et al. |
| 5,874,500 A | 2/1999 | Rhee et al. |
| 5,879,688 A | 3/1999 | Coury et al. |
| 5,888,493 A | 3/1999 | Sawaya |
| 5,900,245 A | 5/1999 | Sawhney et al. |
| 5,932,462 A | 8/1999 | Harris et al. |
| 5,936,035 A | 8/1999 | Rhee et al. |
| 5,972,375 A | 10/1999 | Truter et al. |
| 5,973,014 A | 10/1999 | Funk et al. |
| 5,981,607 A | 11/1999 | Ding et al. |
| 6,017,301 A | 1/2000 | Schwartz et al. |
| 6,031,148 A | 2/2000 | Hayes et al. |
| 6,046,305 A | 4/2000 | Choi |
| 6,051,248 A | 4/2000 | Sawhney et al. |
| 6,060,534 A | 5/2000 | Ronan et al. |
| 6,063,061 A | 5/2000 | Wallace et al. |
| 6,071,875 A | 6/2000 | Clark et al. |
| 6,082,362 A | 7/2000 | Webb |
| 6,083,524 A | 7/2000 | Sawhney et al. |
| 6,121,341 A | 9/2000 | Sawhney et al. |
| 6,123,667 A | 9/2000 | Poff et al. |
| 6,129,761 A | 10/2000 | Hubbell et al. |
| 6,132,986 A | 10/2000 | Pathak et al. |
| 6,149,614 A | 11/2000 | Dunshee et al. |
| 6,149,931 A | 11/2000 | Schwartz et al. |
| 6,153,211 A | 11/2000 | Hubbell et al. |
| 6,154,671 A | 11/2000 | Parel et al. |
| 6,154,971 A | 11/2000 | Parel et al. |
| 6,156,345 A | 12/2000 | Chudzik et al. |
| 6,156,531 A | 12/2000 | Pathak et al. |
| 6,165,201 A | 12/2000 | Sawhney et al. |
| 6,165,489 A | 12/2000 | Berg et al. |
| 6,179,862 B1 | 1/2001 | Sawhney et al. |
| 6,187,330 B1 | 2/2001 | Wang et al. |
| 6,196,993 B1 | 3/2001 | Cohan et al. |
| 6,214,966 B1 | 4/2001 | Harris |
| 6,258,351 B1 | 7/2001 | Harris |
| 6,287,588 B1 | 9/2001 | Shih et al. |
| 6,306,418 B1 | 10/2001 | Bley |
| 6,312,725 B1 | 11/2001 | Wallace et al. |
| 6,331,313 B1 | 12/2001 | Wong et al. |
| 6,413,539 B1 | 7/2002 | Shalaby |
| 6,416,778 B1 | 7/2002 | Ragavan et al. |
| 6,436,424 B1 | 8/2002 | Vogel et al. |
| 6,475,477 B1 | 11/2002 | Kahn et al. |
| 6,475,508 B1 | 11/2002 | Schwartz et al. |
| 6,534,591 B2 | 3/2003 | Rhee et al. |
| 6,544,503 B1 | 4/2003 | Vanderhoff et al. |
| 6,566,406 B1 | 5/2003 | Pathak et al. |
| 6,569,463 B2 | 5/2003 | Patel et al. |
| 6,596,471 B2 | 7/2003 | Pathak et al. |
| 6,605,294 B2 | 8/2003 | Sawhney |
| 6,624,245 B2 | 9/2003 | Wallace et al. |
| 6,632,457 B1 | 10/2003 | Sawhney |
| 6,660,301 B1 | 12/2003 | Vogel et al. |
| 6,660,827 B2 | 12/2003 | Loomis et al. |
| 6,673,093 B1 | 1/2004 | Sawhney |
| 6,689,148 B2 | 2/2004 | Sawhney et al. |
| 6,703,047 B2 | 3/2004 | Sawhney et al. |
| 6,709,668 B2 | 3/2004 | Won et al. |
| 6,818,018 B1 | 11/2004 | Sawhney |
| 6,887,974 B2 | 5/2005 | Pathak |
| 6,958,212 B1 | 10/2005 | Hubbell et al. |
| 6,962,979 B1 | 11/2005 | Rhee |
| 7,009,034 B2 | 3/2006 | Pathak et al. |
| 7,048,946 B1 | 5/2006 | Wong et al. |
| 7,049,346 B1 | 5/2006 | Van Bladel et al. |
| 7,112,239 B2 | 9/2006 | Ahola et al. |
| 7,112,339 B2 | 9/2006 | Ahola et al. |
| 7,211,651 B2 | 5/2007 | Pathak |
| 7,220,270 B2 | 5/2007 | Sawhney et al. |
| 7,413,752 B2 | 8/2008 | Sawhney |
| 7,589,057 B2 | 9/2009 | Chang et al. |
| 7,648,713 B2 | 1/2010 | Sawhney |
| 7,790,141 B2 | 9/2010 | Pathek et al. |
| 7,993,634 B2 | 8/2011 | Hughes et al. |
| 8,088,407 B2 | 1/2012 | Wong |
| 8,492,334 B2 | 7/2013 | Lavik et al. |
| 9,125,807 B2 | 9/2015 | Sawhney et al. |
| 9,370,485 B2 | 6/2016 | Sawhney et al. |
| 9,775,906 B2 | 10/2017 | Sawhney et al. |

(56) References Cited

U.S. PATENT DOCUMENTS

| | | |
|---|---|---|
| 2002/0071869 A1 | 6/2002 | Bures et al. |
| 2003/0091513 A1 | 5/2003 | Mohsen et al. |
| 2003/0100666 A1 | 5/2003 | DeGroot et al. |
| 2003/0143280 A1 | 7/2003 | El-Sherif et al. |
| 2003/0185892 A1 | 10/2003 | Bell et al. |
| 2004/0037889 A1 | 2/2004 | Richeal et al. |
| 2004/0076602 A1 | 4/2004 | Harris |
| 2004/0086548 A1 | 5/2004 | St. John et al. |
| 2004/0116524 A1 | 6/2004 | Cohen et al. |
| 2004/0133275 A1 | 7/2004 | Mansmann |
| 2004/0175410 A1 | 9/2004 | Ashton et al. |
| 2004/0197414 A1 | 10/2004 | Ahola et al. |
| 2005/0043220 A1 | 2/2005 | Guyer et al. |
| 2005/0074497 A1 | 4/2005 | Schultz |
| 2005/0089545 A1 | 4/2005 | Kuwano et al. |
| 2005/0158392 A1 | 7/2005 | Kim et al. |
| 2005/0169882 A1 | 8/2005 | Lowe et al. |
| 2005/0255144 A1 | 11/2005 | Schultz |
| 2006/0002963 A1 | 1/2006 | Rabinovich-Guilatt et al. |
| 2006/0039979 A1 | 2/2006 | Yamada et al. |
| 2006/0057222 A1 | 3/2006 | Linhardt et al. |
| 2006/0100288 A1 | 5/2006 | Bague et al. |
| 2006/0182771 A1 | 8/2006 | Dor et al. |
| 2006/0182781 A1 | 8/2006 | Hughes et al. |
| 2006/0286173 A1 | 12/2006 | Yamada et al. |
| 2007/0185033 A1 | 8/2007 | Gefter et al. |
| 2007/0231366 A1 | 10/2007 | Sawhney et al. |
| 2007/0254038 A1 | 11/2007 | Ducheyne et al. |
| 2007/0264227 A1 | 11/2007 | Lutolf et al. |
| 2007/0275027 A1 | 11/2007 | Wen et al. |
| 2008/0124389 A1 | 5/2008 | Jenkins et al. |
| 2008/0124400 A1 | 5/2008 | Liggins et al. |
| 2008/0132444 A1 | 6/2008 | Li et al. |
| 2008/0171091 A1 | 7/2008 | Wood et al. |
| 2008/0187568 A1 | 8/2008 | Sawhney |
| 2008/0268020 A1 | 10/2008 | Philips et al. |
| 2008/0279944 A1 | 11/2008 | Sawhney |
| 2009/0053276 A1 | 2/2009 | Richard |
| 2009/0105749 A1 | 4/2009 | De Juan et al. |
| 2009/0117188 A1 | 5/2009 | Gershkovich et al. |
| 2009/0240276 A1 | 9/2009 | Ainpour et al. |
| 2009/0252781 A1 | 10/2009 | Sawhney et al. |
| 2009/0264861 A1 | 10/2009 | Jain et al. |
| 2010/0036488 A1 | 2/2010 | De Juan, Jr. et al. |
| 2010/0074957 A1 | 3/2010 | Robinson et al. |
| 2010/0104654 A1 | 4/2010 | Robinson et al. |
| 2010/0209478 A1 | 8/2010 | Sawhney et al. |
| 2011/0142936 A1 | 6/2011 | Campbell et al. |
| 2012/0071865 A1 | 3/2012 | Jarrett et al. |
| 2012/0230913 A1 | 9/2012 | Johnston et al. |

FOREIGN PATENT DOCUMENTS

| | | |
|---|---|---|
| WO | 9835631 | 3/1998 |
| WO | 9903454 | 1/1999 |
| WO | 0130409 | 5/2001 |
| WO | 0219989 | 3/2002 |
| WO | 03031388 | 4/2003 |
| WO | 2006026325 | 3/2006 |
| WO | 2007005249 | 1/2007 |
| WO | 2008117268 | 10/2008 |
| WO | 2010093873 | 8/2010 |
| WO | 2011075557 | 6/2011 |
| WO | 2011112996 | 9/2011 |
| WO | 2011/123416 | 10/2011 |
| WO | 2013/086015 | 10/2011 |

OTHER PUBLICATIONS

Hoare et al., "Hydrogels in drug delivery: progress and challenges", ScienceDirect Polymer, 49:1993-2007 (2008).

Kimura et al., "Injectable Microsphers with Controlled Drug Release for Glaucoma Filtering Surger", Invest. Opthalmol & Visual Sci., 33(12): 3436-3441 (Nov. 1992).

Nihant et al., "Polylactide Microparticles Prepared by Double Emulsion-Evaporation", Journal of Colloid & Interface Science, 173:55-65 (1995).

Reddy et al., "Polyurethane Microspheres as Drug Carriers", Macromolecular Reports, A32(suppls. 5& 6):789-799 (1995).

Sawhney et al., "Bioerodible Hydrogels Based on Photopolymerized Poly(ethylene glycol)-co-poly(α-hydroxy acid) Diacrylate Macromers," Macromolecules, 26:581-587 (1992).

Sharma et al. "Polyethylene Glycol-Induced Precipitation of Interferon Alpha-2a Followed by Vacuum Drying: Development of a Novel Process for Obtaining a Dry, Stable Powder", AAPS PharmSci, 6(1), 14 Pages (Jan. 26, 2004).

Wu et al. "Polymer-Based Sustained-Release Dosage Forms for Protein Drugs, Challenges, and Recent Advances", AAPS PharmSciTech, 9(4):1218-1229 (Dec. 2008).

Yasukawa et al., "Biodegradable Scleral Plugs for Vitreoretinal Drug Delivery", Advanced Drug Delivery Review, vol. 52:25-36 (2001).

Al-Aswad "Another Role for Avastin? Neocasculat Glaucoma" Review of Ophthalmology Online, http://www-revophth.com/content/d/cover_focus/i/1304/c/25094/(accessed Oct. 22, 2012), Jun. 13, 2006, 5 pages.

Jain et al. "Lessons from phase III clinical trials on anti-VEGF therapy for cancer" Nature Clinical Practice Oncology, vol. 3(1):24-40 (Jan. 2006).

Thrimawithana et al., "Drug Delivery to the Posterior Segment of the Eye", Drug Discovery Today, vol. 16 (5/6), 8 pages (Mar. 2011).

File History for U.S. Pat. No. 9,775,906 dated Oct. 3, 2017, 246 Pages.

International Search Report and Written Opinion from corresponding PCT application PCT/US2012/067978, 11 pages, dated Mar. 22, 2013.

\* cited by examiner

US 10,905,765 B2

MEDICAL ORGANOGEL PROCESSES AND COMPOSITIONS

CROSS REFERENCE TO RELATED APPLICATIONS

This application is a Divisional of U.S. patent application Ser. No. 13/705,808 filed Dec. 5, 2012 which claims priority to U.S. Provisional Application No. 61/566,768 filed Dec. 5, 2011, which are hereby incorporated by reference herein.

TECHNICAL FIELD

The technical field generally relates to controlled release of drugs, and includes delivery of proteins from small particles.

BACKGROUND

Therapeutic agents require a means of delivery to be effective. Drug delivery relates to administering a pharmaceutical compound to achieve a therapeutic effect in humans or animals. Delivery mechanisms that provide release of an agent over time are useful. Drug delivery technologies can help to modify a drug release profile, absorption, distribution or drug elimination for the benefit of improving product efficacy and safety, as well as patient convenience and compliance.

SUMMARY

Despite a great deal of research in these arts, the usefulness and success of therapies using biologics, including proteins, continues to be quite limited because of poor stability of the biologic in vivo. Despite conventional wisdom that proteins should not be exposed to organic solvents in pharmaceutical processing techniques, it has been observed that many solvents can be used. Methods that use such solvents are described, including embodiments for two-solvent delivery systems with the first solvent being an organic solvent in processing and the second solvent being physiological fluids in vivo.

An embodiment of the invention is a xerogel that comprises a protein powder, or other water soluble biologic powder, dispersed in a matrix of the xerogel. The xerogel may be hydrated at the point of use and placed in a tissue, where it controllably releases the protein over time. This embodiment and others are detailed below.

DETAILED DESCRIPTION OF PREFERRED EMBODIMENTS

An embodiment of the invention is a xerogel that comprises a protein powder, or other water soluble biologic powder, dispersed in a matrix of the xerogel. The xerogel may be hydrated at the point of use and placed in a tissue, where it controllably releases the protein over time. The powder contains fine particles of protein. The xerogel matrix, upon hydration, is a hydrogel made of a crosslinked matrix. The protein is in a solid phase and is substantially not soluble until the matrix begins to erode, thereby allowing the protein to go into solution. The matrix protects the protein from cells, enzymatic denaturation, and unwanted local reactions. The protein is in a substantially solid phase until released by gradual solvation and is thus protected from denaturation, autohydrolysis, proteolysis, and local chemical reactions that can cause a loss of effectiveness or create antigenicity.

Figure 1A:
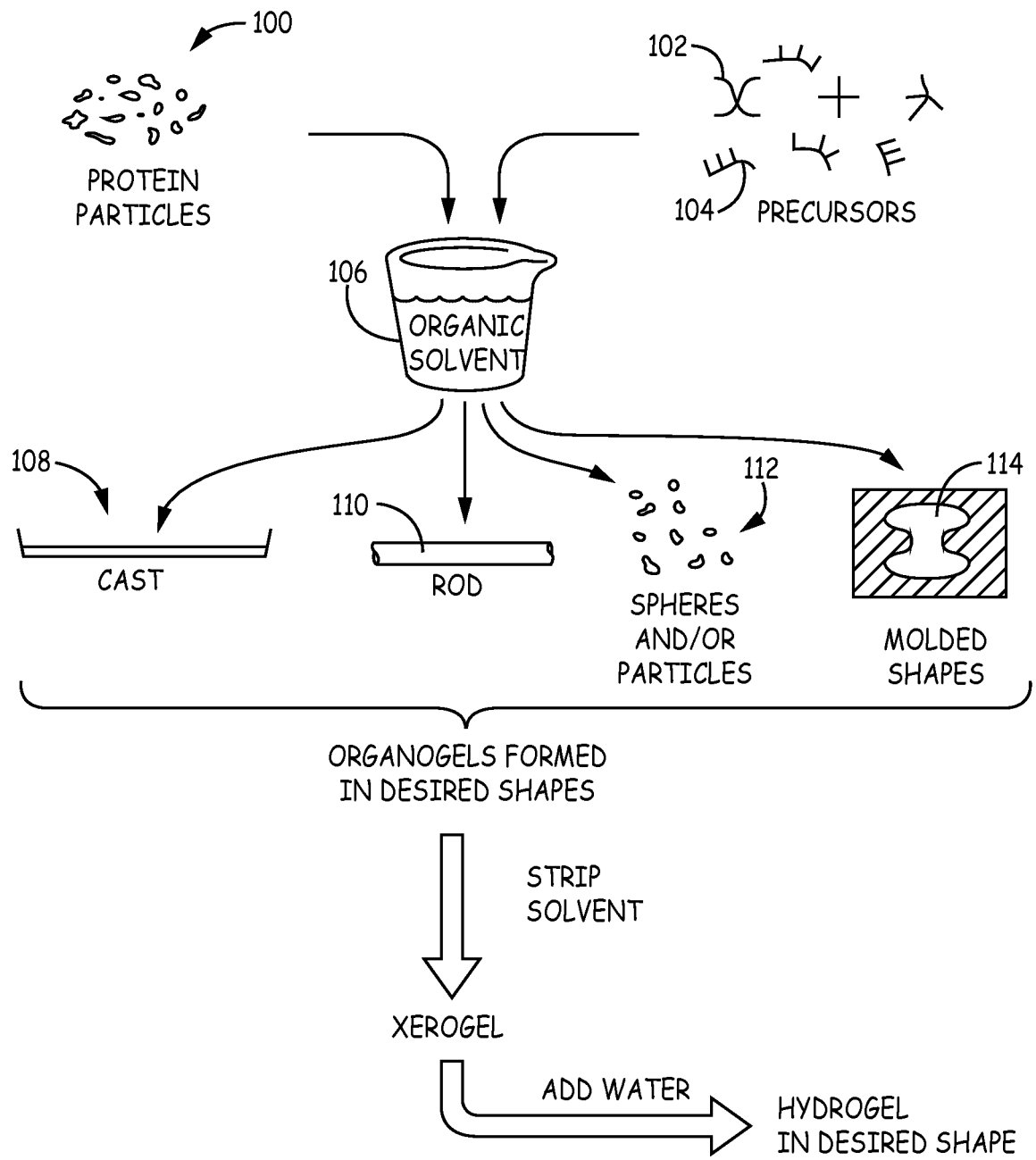
FIG. 1A depicts formation of a biomaterial.
Figure 1B:
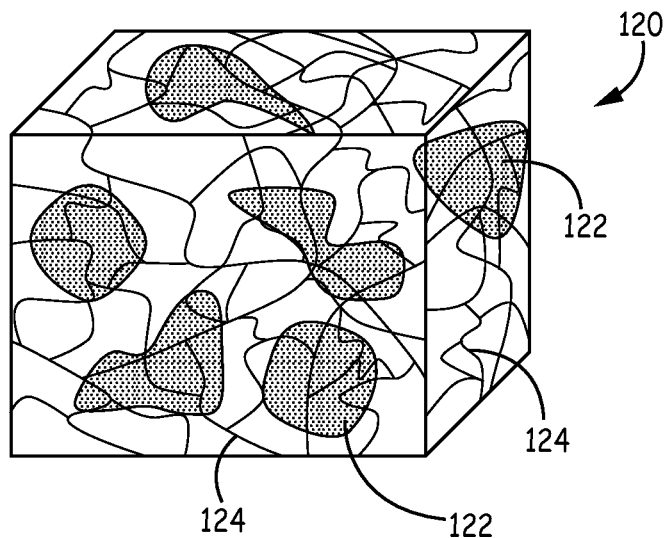
FIG. 1B depicts a microstructure of the biomaterial of FIG. 1A.

FIG. 1A depicts an embodiment of this process, which is started with protein particles 100 that have been prepared by conventional means to preserve protein secondary and, if present, tertiary or quaternary structure. These are combined with precursors 102, 104, into organic solvent 106. The mixture is processed to achieve the desired shape of the biomaterial, e.g., by casting 108, as rod 110, as particles and/or spheres 112, and molded shapes 114. The solvent is stripped out of the shapes and the materials will form hydrogels when exposed to water. The entire process, until the point where the xerogel is actually used with a patient, may be performed in an absence of water and/or in an absence of hydrophobic materials. FIG. 1B depicts a microstructure of a biomaterial 120 made by this process. The structure is representative of the material across the process of its manufacture and use: organogel, xerogel, and then hydrogel. The crosslinked matrix is made of precursors 124 that have been covalently reacted with each other. Particles 122 of a water soluble biologic are dispersed within the matrix. The matrix is a continuous phase and the particles are spread out inside it and are the discontinuous phase, also referred to as the dispersed phase.

Figure 1C:
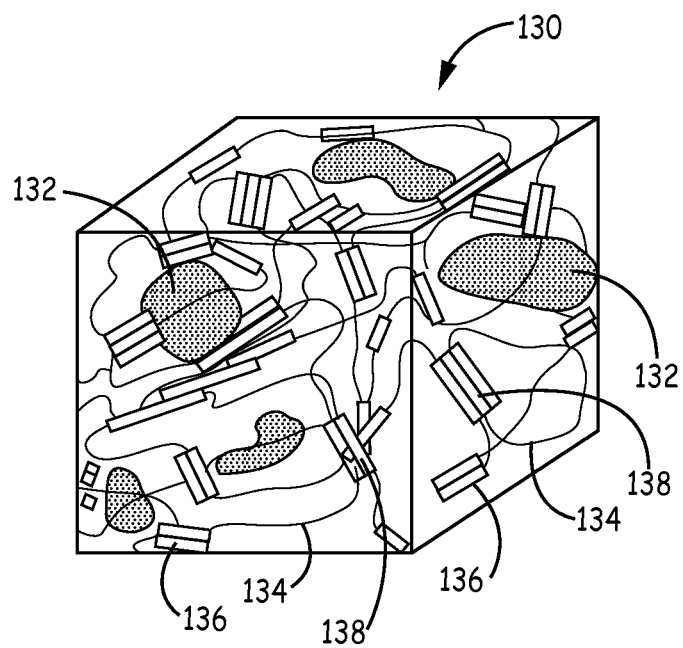
FIG. 1C depicts a microstructure of an alternative embodiment of a biomaterial.
Figure 2A:
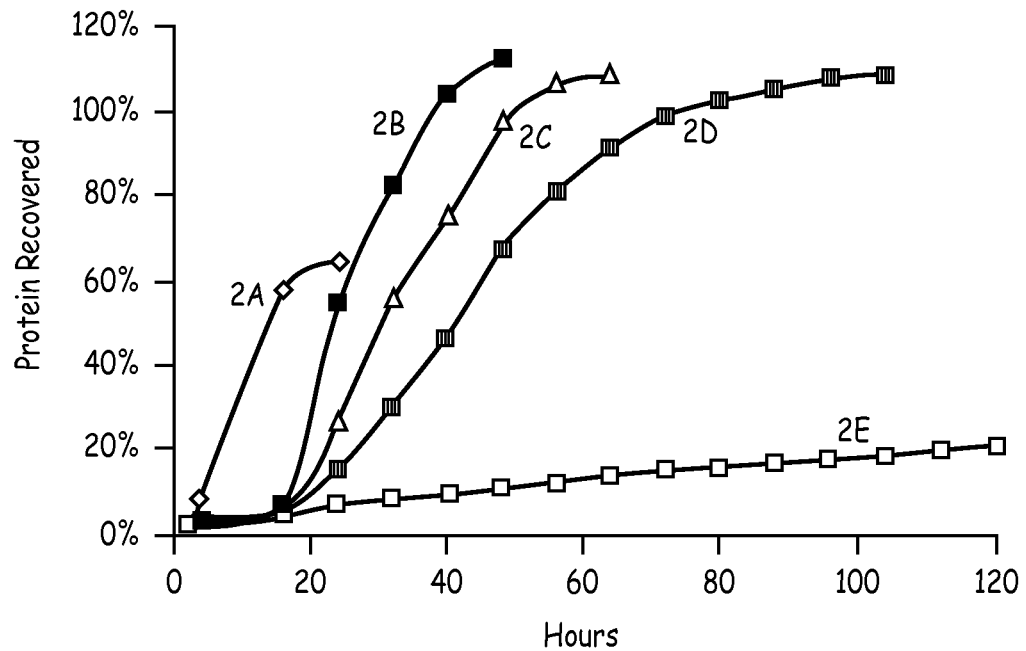
FIG. 2A is a plot of HPLC data showing release of ovalbumin over time in physiological solution at 37° C.
Figure 2B:
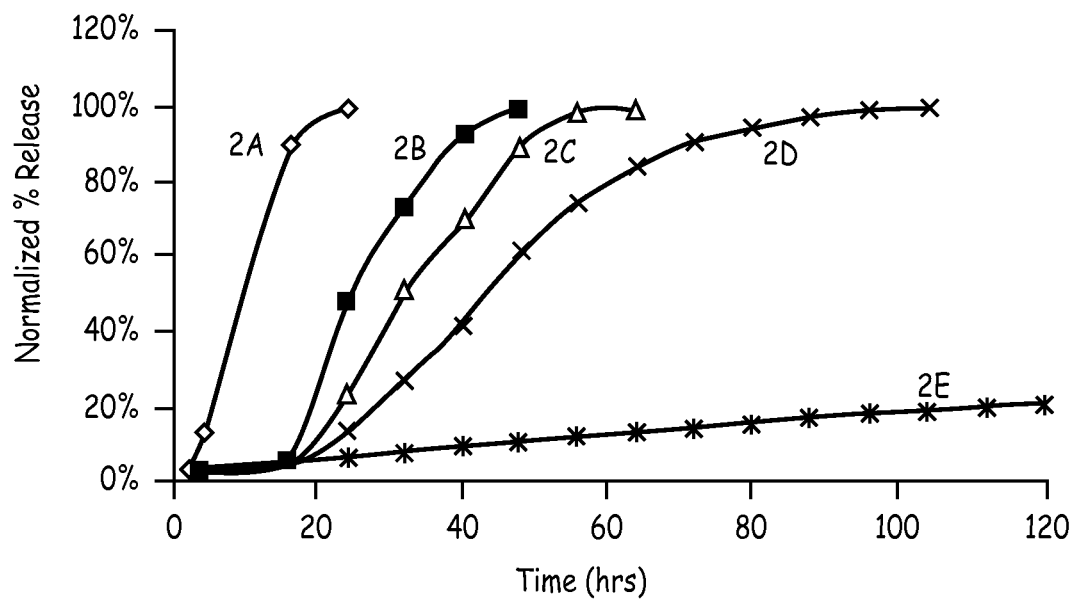
FIG. 2B is a plot of the data of FIG. 2A after being normalized to the protein level at complete dissolution of the hydrogel.
Figure 3:
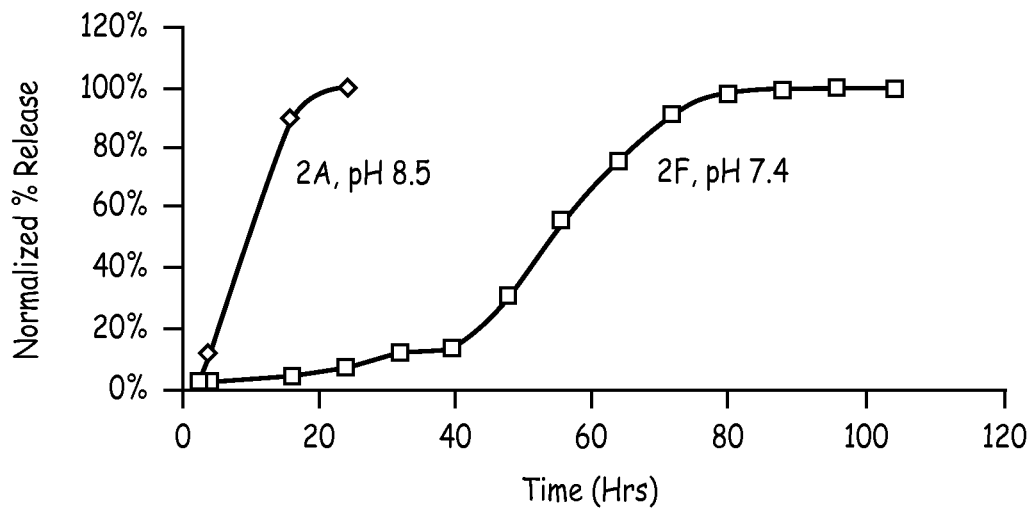
FIG. 3 is a plot of HPLC data showing release of ovalbumin over time in physiological solution at pH 8.5 and 37° C. and in physiological solution at pH 7.4 and 37° C. Data are normalized to the protein level at complete dissolution.
Figure 4:
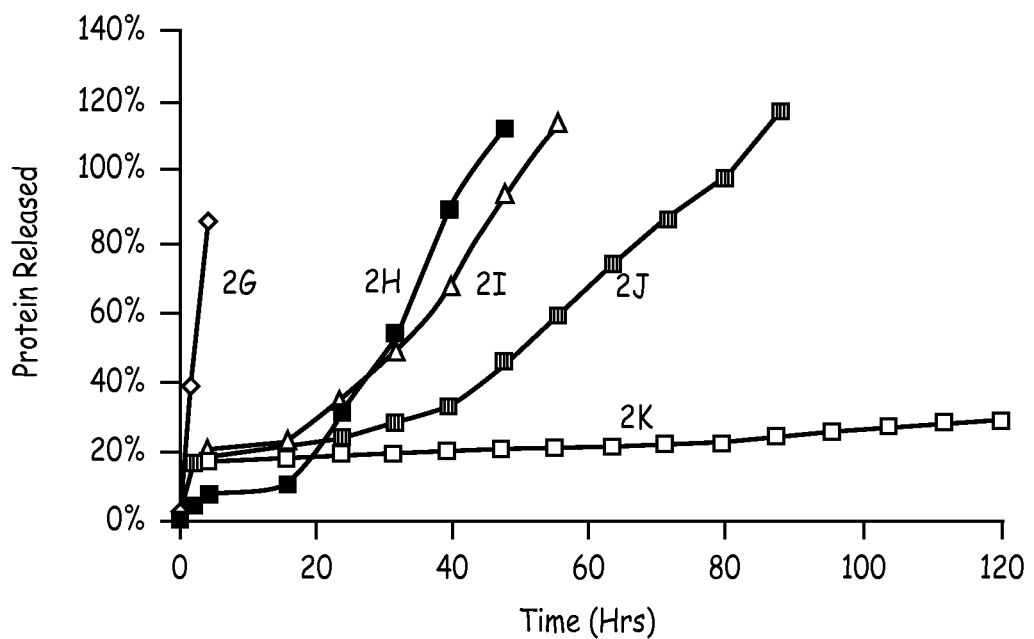
FIG. 4 is a plot of HPLC data showing release of IgG over time in physiological solution at 37° C.
Figure 5:
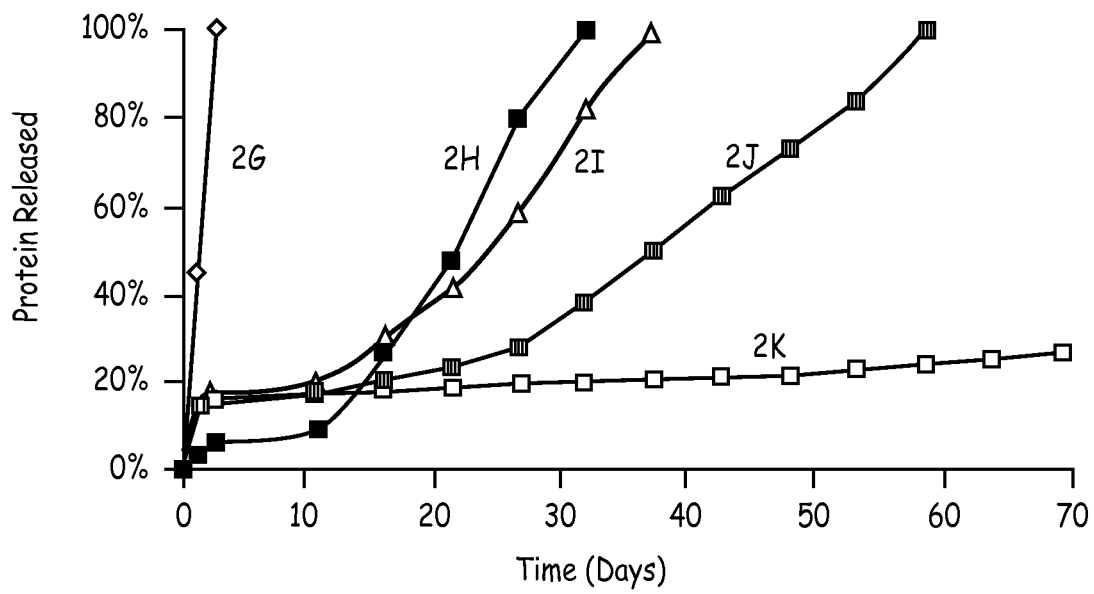
FIG. 5 is a plot of the data of FIG. 4 after being normalized to the protein level at complete dissolution of the hydrogel.

Alternative embodiments involve using block copolymer precursors that are physically crosslinked by formation of hydrophobic domains, as depicted in FIG. 1C. The biomaterial 130 has biologic particles 132 dispersed in the matrix. The precursors have hydrophilic blocks 134 and hydrophobic blocks 136. The hydrophobic blocks 136 self-assemble to form hydrophobic domains 138, which create physical crosslinks between the precursors. The term physical crosslink means a non-covalently bonded crosslink. Hydrophobic domains are one such example, as well as the hard-and-soft segments of a polyurethane or other segmented copolymers. Ionic crosslinks are another example. The term crosslink is well understood by artisans, who will immediately be able to distinguish covalent crosslinks from physical cross links, as well as the subtypes of physical crosslinks such as ionic, hydrophobic, and crystalline domains.

Other drug delivery approaches have encapsulated proteins with, for example, liposomes or micelles, or made nanoparticles that use polymers or other agents in creation of the particles. Protein delivery in a hydrogel has been generally directed to sequestering the proteins from the hydrogel: for example, by placing the hydrogel in a liposome, micelle, or in a mixture with a binding agent such as a polymer. Other approaches have been directed to directly adsorbing materials to proteins so as to inhibit their dissolution. Another approach was to precipitate proteins in the delivery process, as disclosed in U.S. Publication No. 2008/0187568. Other approaches use hydrogels with soluble proteins dispersed through the hydrogel, with hydrogel erosion controlling the release.

Despite all of these efforts, the usefulness and success of sustained release therapies using biologics, including proteins, is limited because the stability of the biologic in vivo tends to be poor. And a loss of conformation can lead not only to a loss of efficacy, but it can be detrimental by causing unwanted effects or eliciting an immune response. Despite very many efforts, there have been no generally applicable solutions effective enough to have real-world clinical value, as documented in Wu and Jin, *AAPS PhamSciTech* 9(4): 1218-1229 (2008).

Surprisingly, however, the embodiments provided herein show that protein or other biologic solubility and release from a matrix can be controlled by disposing a biologic as a solid-phase particulate in a suitable matrix so that these other approaches involving polymers, encapsulants, binders, and the like are not needed. Further, the biologic resists denaturation even in aqueous in vivo environments. The particulates in the matrices are water soluble but, despite not having any coatings or the like, are slow to dissolve and their dissolution in physiological solution, which would normally be measured in minutes or hours, can be extended to days, weeks, or months. Moreover, another unexpected and surprising result has been observed: namely, that the biologics do not tend to aggregate even though they are necessarily present at very high concentrations within the matrix. It seems that the biologics come off of the particles very slowly. A first theory of operation, to which the invention is not to be limited, is that the molecular strands of the matrix which are made of highly mobile polymers, for example polymers such as polyethylene glycol (PEG) or polyethyleneimine-form an exclusion volume around themselves, which limits the solubility of any other macromolecule in the immediate vicinity. This structural attribute not only confines the proteins in the solid phase by physical entrapment within the matrix, but also limits the dissolution of the macromolecule, so that the protein particle is unable to move into solution; as the particles and proteins begin to swell by solvation with water, they are restrained by the matrix until the matrix is at least partially dissolved. Thus, as the crosslink density decreases and the molecular strands move further apart, gradual dissolution of the entrapped macromolecule particle is facilitated. These processes thus provide an unexpected and surprising result: the biologics stay in the solid phase until they are getting relatively close to the time of their release from the matrix: consequently, the protein or other biologic is stable because it is not exposed to the detrimental effects of being in solution for a long time. Release is also restricted by the diffusion of the macromolecule out from the matrix and is influenced by the molecular weight of the macromolecule as well as the characteristics of the matrix forming polymers. A second theory of operation is complementary to the first and is likewise not a mechanism to which the invention is to be limited: the molecular strands of the matrix are associating with water molecules near the proteins such that the proteins are unable to dissolve. This second theory is applicable to polymers with highly mobile, hydrophilic, linear chains such as PEG. Besides PEG, other water soluble polymers or copolymers that exhibit an exclusion volume effect with the selected protein can be chosen. For instance, polymers such as polyacrylic acid, polyvinyl alcohol, polyvinylpyrrolidone (PVP), and polyhydroxyethlymethacrylate (PHEMA) will generally have such an effect. Some polysaccharides also have these effects. PEG and/or these other polymers can also be incorporated as solids in the organogel. They will solubilize in the presence of water, i.e., in the hydrogel. Moreover, non-crosslinked PEG and/or PEG copolymers such as a PLURONIC be additives that can be trapped in the hydrogel along with the protein to enhance the exclusion volume effect, thereby keeping the proteins in the solid state.

An aspect of the systems disclosed herein relates to a large increase in control over the time of release caused by placing protein particles in a hydratable xerogel. Examples 1-2 detail processes used to form xerogels containing particles of water soluble biologics. The proteins albumin and immunoglobulin (IgG) were used to model a water soluble therapeutic agent protein. Powders of these proteins were prepared. The powder particles were combined with hydrogel precursors in organic solvents to form an organogel. Tables 1-5 of Example 1 set forth examples of the organogels comprising the dispersed protein powder. The organogels were broken up and sieved into collections of particles that were evacuated of organic solvents to form xerogels. Working Example 2 documents release of the proteins from the xerogels.

As illustrated in FIGS. 2-5, the proteins were fully released; unexpectedly, there was no detectable reaction of the organogel precursors with the proteins that prevented them from being solubilized as the matrix degraded. In fact, these proteins, and proteins in general, contained amine and thiol functional groups that are potentially very reactive towards strong electrophiles such as the electrophilic precursors that were used. Although a reaction with these electrophilic functional groups was expected, the lack of reaction indicates that these reactions were prevented by leaving the proteins in a non-dissolved or substantially solid phase while the gel-forming precursors were in a liquid phase prior to gelation. The release curves showed good control over the rate of release, and ranged from a quick release of hours to months of release.

Figure 6:
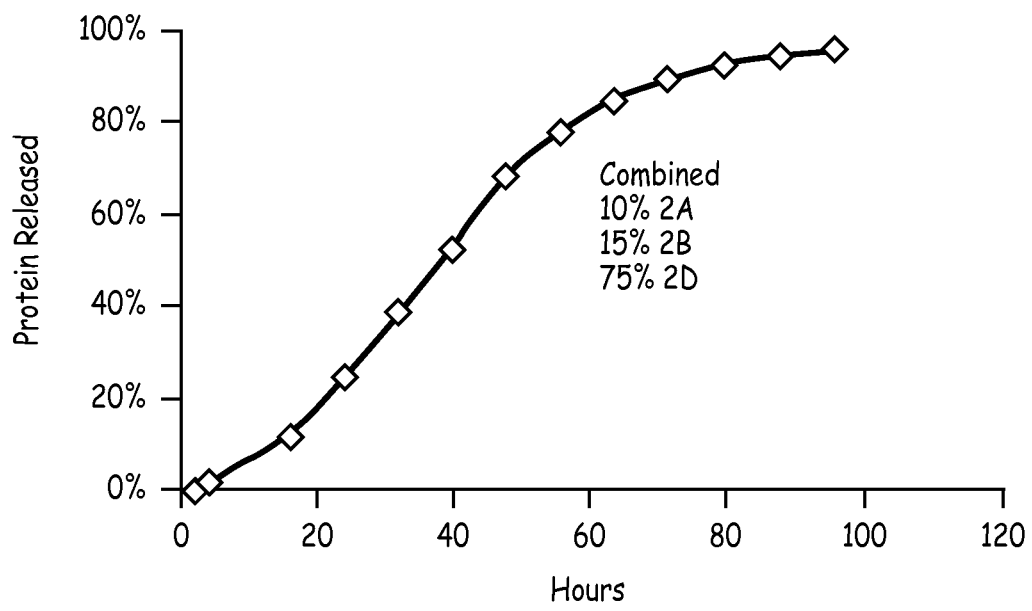
FIG. 6 is a plot depicting a calculated release profile of albumin from a combination of hydrogel vehicles.
Figure 7:
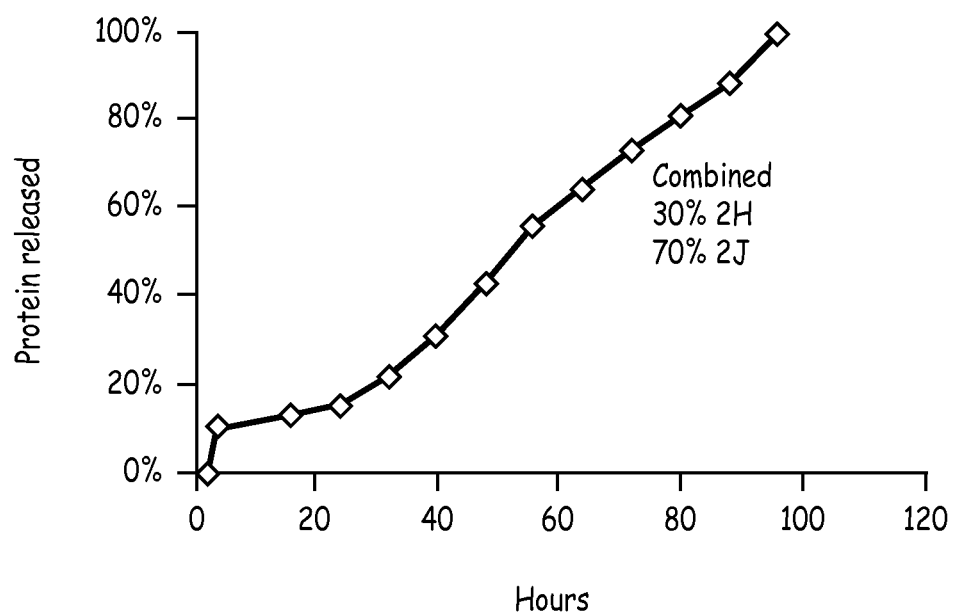
FIG. 7 is a plot depicting a calculated release profile of albumin from a combination of hydrogel vehicles.

Moreover, the rate and kinetics of release may be further controlled by combining the various sets of particles with each other, as illustrated in FIGS. 6 and 7. These demonstrate a substantially zero order release, which is the ability to deliver a drug at a rate which is independent of time and the concentration of drug within a pharmaceutical dosage form is desirable. A zero order release mechanism ensures that a steady amount of drug is released over time, minimizing potential peak/trough fluctuations and side effects, while maximizing the amount of time the drug concentrations remain within the therapeutic window (efficacy).

Processes and Materials for Preparing an Organogel-Hydrogel, Two-Solvent Delivery System for Water Soluble Biologics A first embodiment involves forming covalently crosslinked matrices. A fine powder of a water soluble biologic is prepared and suspended in an organic solvent that does not solvate the water soluble biologic, e.g., protein. The term powder is used broadly herein to refer to a collection of dry particles. The term particles is broad and includes spheres, teardrop-shapes, small rods and other irregular shapes. In general, the powder has been processed to provide a controlled particle composition with a known size, shape, and distribution (variance from a mean or average) thereof. Protein powders typically contain stabilizing sugars such as sucrose or trehalose. These sugars are generally water soluble and not organic soluble. It was found that these will remain with the protein through the process until the point of hydration to form the hydrogel. Matrix precursors are prepared that have the capacity to form a crosslinked organogel by reacting with each other in the organic solvent. The precursors are chosen to be soluble in the organic solvent. The precursors and water soluble biologic powder are mixed in the organic solvent so that the water soluble biologic particles are dispersed through the matrix that forms upon formation of covalent bonds between the precursors. The matrix formed in the organic solvent is referred to as an organogel. The solvent is removed to form a xerogel. Upon hydration in water the matrix forms an internally covalently crosslinked hydrogel. This process is a serial two-solvent process because the organic solvents have to be effective with the biologic and the precursor(s), strippable (i.e., removable without leaving pharmaceutically unacceptable residue), but the precursors have to be effective in an in vivo aqueous environment. At no time is the protein exposed to both organic and aqueous phases. Exposure of proteins in aqueous solution to interfaces such as with organic liquids or solids or air bubbles is believed to contribute to protein adsorption and denaturation. The organogel to xerogel to hydrogel serial process eliminates the possibility of interface exposure, i.e., embodiments include processes as described herein being performed without exposure of a water soluble biologic to an interface between any combination of the following: air, gas, water, organic solvent.

Another embodiment is the formation of a covalently crosslinked gel (also referred to herein as a pseudo-organogel) by employing liquid reactive polymers as matrix precursors. Matrix precursors are prepared that have the capacity to form a crosslinked organogel by reacting with each other in the absence of organic solvent, e.g. when in the molten state. The precursors and water soluble biologic powder are mixed at a temperature high enough to liquefy the precursor polymers, but low enough to maintain protein stability. Examples of such temperatures are from about 10° C. to about 75° C., or up to about 60° C. or up to about 75° C.; artisans will immediately appreciate that all values and ranges between the explicitly stated values are contemplated and are incorporated herein as if written in detail. Mixing conditions are employed such that the water soluble biologic particles are dispersed through the matrix that forms upon formation of covalent bonds between the precursors. The reaction is thus performed in a melt of the polymers, with the term melt meaning that no solvents are present. There may be, however, other materials in the melt, e.g., biologics, sugars, proteins, buffers. Embodiments include material and a process of making a medical material comprising forming a gel around a powder of a water soluble biologic, with the powder being dispersed in the gel, wherein forming the gel comprises preparing a melt of one or more precursors and covalently crosslinking the precursors. Said gel may have a large portion of its volume occupied by the biologic or other solids (e.g., sugars, buffer salts), e.g., from about 30% to about 95% v/v; artisans will immediately appreciate that all values and ranges between the explicitly stated values are contemplated and are incorporated herein as if written in detail, e.g., at least 30% v/v or from about 40% to about 75%.

Another embodiment of the serial two-solvent process involves forming a crosslinked material having physical crosslinks. One such embodiment uses block copolymers as precursors. The precursors have a lyophilic (solvent-loving) block and a lyophobic (solvent-hating) block. These precursor(s) are added to the organic solvent and from a physically crosslinked matrix. The blocks (also referred to as segments) that precipitate in a specific organic solvent to form the organogel may or may not be the same segments that precipitate in water to form the hydrogel. After stripping the solvent, the resultant xerogel forms a hydrogel in aqueous solution because one or more block or segment portions are hydrophobic and one or more block or segment portions are hydrophilic. A related embodiment uses two organic solvents: the block copolymeric precursor is dissolved in a first organic solvent. The copolymer solution is then mixed with a second organic solvent that is miscible with the first solvent, but is a non-solvent for the at least one of the segments of the copolymer. The lyophobic domains form the organogel. Another embodiment uses the first and second organic solvent and uses the second organic solvent to also precipitate the biologic, such that the organogel and the particles of the biologic are formed at the same step.

Another embodiment of the serial two-solvent process involves thermal gelation. A precursor that transitions from solution to an organogel in the organic solvent at temperatures in a range of about −20° C. to about 70° C. is placed with the biologics in the organic solvent at a temperature wherein the precursor is in solution. The solution is then cooled to a second temperature below the gelation point, and the precursor forms an organogel. Accordingly, a process for making an organogel is to heat a solvent to dissolve a copolymer and then cool the solution to precipitate at least one of the segments of the copolymer. The solvent is then stripped to make a xerogel. The precursors are chosen so that the xerogel is a hydrogel at physiological temperatures.

Block copolymers adaptable for use in these processes include many copolymers of PEG. The PEG is hydrophilic and is lyophilic for many organic solvents. Other hydrophilic polymers and polymeric segments are polyvinyl alcohol, polyacrylic acid, polymaleic anhydride, PVP, PHEMA, polysaccharides, polyethylene imine, polyvinyl amine polyacrylamide(s), and the like. The other block is chosen to be hydrophobic and lyophobic for the organic solvent. Examples of these other blocks are: polybutylene terephthalate (PBT), polylactic acid, polyglycolic acid, polytrimethylene carbonate, polydioxanone, and polyalkyl ethers such as polypropylene oxide (PLURONICS, POLOXAMERS). The copolymers may have one or more of each kind of block.

These processes may be performed so that the water soluble biologic never contacts water from the time it is initially prepared until placed in vivo. The water soluble biologic may be further processed so that, once obtained in a purified form at the source or a manufacturing site, it is not thereafter dissolved in and/or is never exposed to water during the gel manufacturing process. Exposure to water can cause a variety of problems. One problem is that a protein will undergo hydrolysis over time so that it is slowly degraded. Another problem is that a protein, once it is in solution, can rearrange or form quasi-stable aggregates such as dimers or trimers.

Embodiments of the inventions include these process performed in the absence of hydrophobic polymers and/or hydrophobic solvents. The embodiments that require a hydrophobic block polymer cannot be performed in a hydrophobic-free process, but the artisan can readily discern which processes are applicable. One embodiment provides for hydrophilic precursors to be covalently crosslinked in the organic solvent in the presence of a biologic particle and an absence of hydrophobic materials, both at the organogel steps and subsequent steps. In some embodiments a solvent that is hydrophobic might be present without detriment, depending on the solvent, so embodiments include an absence of hydrophobic materials other than solvents; and/or an absence of hydrophobic polymers; and/or an absence of hydrophobic polymer segments.

Conventional wisdom teaches that organic solvents generally denature proteins. Some life sciences processes can tolerate some degree of denaturation, for example, in diagnostic or analytical settings. In the medicinal arts, however, even a small degree of denaturation is undesirable. Denatured proteins can exhibit a wide range of characteristics, from loss of solubility to communal aggregation. Communal aggregation involves aggregation of the hydrophobic proteins to come closer to each other to reduce the total area exposed to water. A reduction in distance can cause permanent or quasi-stable associations. When a protein is denatured, its secondary and tertiary structures are altered but the peptide bonds of the primary structure between the amino acids are generally left intact.

Surprisingly, however, it has been discovered that proteins left in a solid phase can be exposed to certain organic solvents without extensive denaturation. Fully anhydrous organic solvents handled under anhydrous conditions are preferred. Denaturation from exposure to organic solvents may happen when the protein is already in an aqueous solution and/or if the organic solvent, or organic/aqueous mixed solvent (e.g. ethanol/water), has a propensity to dissolve or even in a limited way, swell, the protein particle. Protein-solvent compatibility can be established experimentally by exposure followed by characterization testing to determine if the protein has been denatured and/or undergone substitution or alteration of one or more chemical groups. Organic solvent compatibility can be tested simply by immersing the subject protein in the subject solvent for an appropriate period of time, removing the protein, such as by filtration and vacuum drying, and then testing for recovery of the protein by HPLC or other appropriate analytical method. Solvents most likely to leave the protein unharmed are anhydrous and hydrophobic, but must also be good solvents for the gel forming precursor molecules. In the case of polyethylene glycol (PEG) precursors, solvents such as methylene chloride and dimethyl carbonate have been employed. Other solvents such as acetone (or acetone/water), ethyl acetate, tetrahydrofuran, may also be useful. Supercritical fluid solvents such as carbon dioxide may also be useful for forming organogels.

The precursors are described in detail elsewhere herein. Many useful precursors are available as a plurality of precursors. A first precursor is added to the solvent-protein mixture, followed by a second precursor that is reactive with the first precursor to form crosslinks. The first precursor may be chosen to have only those functional groups that are unreactive to form covalent bonds with a protein in the absence of further chemical components. Proteins have amines and thiols that may be used to react with certain electrophilic functional groups to form covalent bonds, as well as carboxyls and hydroxyls that are available for other chemical reactions. The precursor may accordingly be chosen to be unreactive with these functional groups. For example, the precursor may have amines and/or thiols and/or hydroxyls and/or carboxyls and be unreactive with proteins. Accordingly, an embodiment of the invention involves adding a first protein-unreactive precursor to a protein-organic solvent mixture and then adding a second precursor that is reactive with the first precursor.

The water soluble biologic particles may be free of one or more of: binders, fatty acids, hydrophobic materials, surfactants, fats, phospholipids, oils, waxes, micelles, liposomes, and nanocapsules. The organogel or xerogel comprising the water soluble biologic particles may also be free of one or more of the same. The protein or other water soluble biologic in the xerogel may all be in a solid phase, may be all crystalline, partially crystalline, or essentially free of crystals (meaning more than 90% free of crystals w/w; artisans will immediately appreciate that all the ranges and values within the explicitly stated ranges are contemplated).

The xerogel-water soluble biologic material may be formed in a desired shape. One method is to react the precursors in a mold that has the desired shape. The shape is removed from the mold before or after removal of the solvent. The material may also be fragmented into particles, as described in more detail elsewhere herein.

After formation of the matrix in the organic solvent, the solvent may be removed to form the xerogel. Potential processes include, e.g., precipitation with non-solvent, nitrogen sweep drying, vacuum drying, freeze-drying, a combination of heat and vacuum, and lyophilization.

If molten precursors are used in the absence of a tertiary solvent, there is no need to employ any solvent removal process. Upon cooling the material forms a rubbery solid (if above Tm), a semirigid semicrystalline material (if below Tm) or a rigid glassy solid (if below Tg). These materials are more dense than xerogels formed from organic solvents. When filled with particles of other materials, e.g., therapeutic agents, buffer salts, visualization agents, they can be highly porous, since the solid particles create and fill the pores.

All of these processes may be performed without the water soluble biologic. Materials, including particles, have usefulness for many applications without the biologic. Uses include, e.g., tissue augmentation, fillers, and tissue separations in radiotherapy.

Moreover, all of these processes may be performed with additional agents instead or, additionally with, the biologics. Such additional agents include visualization agents visible to a naked eye and radiopaque agents or materials.

Particles Preparation

The organogel may be formed and then reduced to particles that are subsequently treated to remove the organic solvent or solvents to form a xerogel. For an injectable form, the organogel can be macerated, homogenized, extruded, screened, chopped, diced, or otherwise reduced to a particulate form. Alternatively, the organogel can be formed as a droplet or a molded article containing the suspended protein particles.

One process for making organogel particles involves creation of a matrix that is broken up to make organogel particles. Thus matrices are made with precursors as described herein and are then broken up. One technique involves preparing the organogel with protein particles and grinding it, e.g., in a ball mill or with a mortar and pestle. The matrix may be chopped or diced with knives or wires. Or the matrix may be cut-up in a blender or homogenizer. Another process involves forcing the organogel through a mesh, collecting the fragments, and passing them through the same mesh or another mesh until a desired size is reached.

The water soluble biologics, e.g., proteins are prepared as particles before dispersal into the organogels. Multiple protein particulation technologies, such as spray drying or precipitation exist and may be employed provided the protein of interest is compatible with such processing. An embodiment of particle preparation involves receiving the biologic without substantial denaturation, e.g., from a supplier or animal or recombinant source. The solid phase is a stable form for the protein. The protein is lyophilized or concentrated or used as received. The protein is then prepared as a fine powder without denaturation by processing it in a solid state and avoiding high temperatures, moisture, and optionally in an oxygen free environment. Powders may be prepared by, for example, grinding, ball milling, cryomilling, microfluidizing or mortar-and-pestle followed by sieving a solid protein. The protein may also be processed in a compatible anhydrous organic solvent in which the protein in question is not soluble, while keeping the protein in a solid form. Particle size reduction to the desired range may be achieved by, for example, grinding, ball milling, jet milling of a solid protein suspension in a compatible organic solvent. High shear rate processing, high pressure, and sudden temperature changes should be minimized as they lead to protein instability. Accordingly, care must be taken to handle the protein or other water soluble biologic in a manner that avoids damage, and the use of routine processes for making particles should not be assumed to be suitable and are not to be expected to be useful without suitable re-engineering and testing of the results.

The term powder of the protein refers to a powder made from one or more proteins. Similarly, powders of water soluble biologics are powders having particles made of one or more water soluble biologics. The proteins in a protein particle or the biologics in a biologics particle are associated with each other to provide mechanical integrity and structure to the dry particle even in the absence of binders or encapsulants. These powders are distinct from protein or biologic delivery using an encapsulation or approach such as a liposome, micelle, or nanocapsule other technique that substantially encapsulates a protein or biologic. The powders and/or xerogels or hydrogels that contain them may be free of encapsulating materials and be free of one or more of a liposome, micelle, or nanocapsule. Further, a protein particle or a water soluble biologic particle may be made that is free of one or more of: binders, non-peptidic polymers, surfactants, oils, fats, waxes, hydrophobic polymers, polymers comprising alkyl chains longer than 4 $CH_2$ groups, phospholipids, micelle-forming polymers, micelle-forming compositions, amphiphiles, polysaccharides, polysaccharides of three or more sugars, fatty acids, and lipids. Lyophilized, spray dried or otherwise processed proteins are often formulated with sugars such as trehalose to stabilize the protein through the lyophilization or other processes used to prepare the proteins. These sugars may be allowed to persist in the particle throughout the organogel/xerogel process. The particles may be made to comprise between about 20% and about 100% (dry w/w) protein; artisans will immediately appreciate that all the ranges and values within the explicitly stated ranges are contemplated, e.g., about 50% to about 80% or at least 90% or at least about 99%.

The particles of biologics or the particles or organogels or the particles of the xerogels may be separated into collections with a desired size range and distribution of sizes by a variety of methods. Very fine control of sizing is available, with sizes ranging from 1 micron to several mm, and with a mean and range of particles sizes being controllable with a narrow distribution. Artisans will immediately appreciate that all the ranges and values within the explicitly stated ranges are contemplated, e.g., from about 1 to about 10 μm or from about 1 to about 30 μm. About 1 to about 500 microns is another such range that is useful, with sizes falling throughout the range and having a mean sizing at one value within the range, and a standard deviation centered around the mean value, e.g., from about 1% to about 100%. A simple method for sizing particles involves using custom-made or standardized sieve mesh sizes. In addition to standard U.S. and Tyler mesh sizes, sieves are also commonly used in the Market Grade, Mill Grade, and Tensile Bolting Cloth. Materials forced through meshes may show deformation so that the particle size is not precisely matched to mesh sizes; nonetheless, mesh sizes may be chosen to achieve a desired a particle size range. Particle size analyzers where the protein particle is dispersed in an organic or oil phase are commonly used. Microscopy is also commonly used to determine particle size. A spheroidal particle refers to a particle wherein the longest central axis (a straight line passing through the particle's geometric center) is no more than about twice the length of other central axes, with the particle being a literally spherical or having an irregular shape. A rod-shaped particle refers to a particle with a longitudinal central axis more than about twice the length of the shortest central axis. Embodiments include making a plurality of collections of particles, with the collections having different rates of degradation in vivo, and mixing collections to make a biomaterial having a degradation performance as desired.

Delivery of Water Soluble Biologics without Denaturation

These processes may be performed with a protein or other water soluble biologics. These include peptides and proteins. The term protein, as used herein, refers to peptides of at least about 5000 Daltons. The term peptide, as used herein, refers to peptides of any size. The term oligopeptide refers to peptides having a mass of up to about 5000 Daltons. Peptides include therapeutic proteins and peptides, antibodies, antibody fragments, short chain variable fragments (scFv), growth factors, angiogenic factors, and insulin. Other water soluble biologics are carbohydrates, polysaccharides, nucleic acids, antisense nucleic acids, RNA, DNA, small interfering RNA (siRNA), and aptamers. Descriptions herein are often set forth in terms of proteins but the methods are generally applicable to other water soluble biologics.

Proteins are easily denatured. As described herein, however, proteins may be delivered substantially without denaturation, including the case wherein no binders, lipophilic materials, surfactants, or other prophylactic components are used. The term substantially without denaturation refers to a protein processed into a particle without modification of the protein's chemical structure (without addition of chemical groups or changes of the existing chemical groups) and without changes to the protein's conformation, i.e., secondary and/or tertiary and/or quaternary structure. The term substantially, in this context, means that no significant differences ($p\text{-value}<0.05$) between processed proteins and control proteins are observed for an averaged test group as tested under routine conditions by enzyme-linked immunosorbent assay (ELISA) for epitope denaturation and by isoelectric focusing (IEF) for a shift of more than 0.2 in isoelectric point (pI), see U.S. patent application Ser. No. 13/234,428, which is hereby incorporated by reference herein for testing or protein stability and all purposes; in case of conflict, the instant specification controls. A primary protein structure refers to the amino acid sequence. To be able to perform their biological function, proteins fold into one or more specific spatial conformations, driven by a number of non-covalent interactions such as hydrogen bonding, ionic interactions, Van Der Waals forces, and hydrophobic packing. The term secondary structure refers to the local protein structure, such as local folding. The tertiary structure refers to a particular three-dimensional conformation, including folding. A protein that has secondary and/or tertiary structure thus exhibits local and general structural organization. In contrast, a linear peptide that has no particular conformation does not have secondary and/or tertiary structure. The term native means as found in nature in vivo, so that proteins may be processed into particles and released in a native conformation.

Proteins may be tested for denaturation by a variety of techniques, including enzyme-linked immunosorbent assay (ELISA), isoelectric focusing (IEF), size exclusion chromatography (SEC), high-pressure liquid chromatography (HPLC), circular dichroism (CD), and Fourier Transform Infrared Spectroscopy (FTIR). These tests report parameters such as changes in molecular weight, change in end groups, changes in bonds, changes in hydrophobicity or volume exclusion, and revelation/hiding of antigenic sites. In general, a test by IEF and ELISA may be designed that is adequate to show native conformation after processing, although other tests and test combinations may alternatively be used.

Experimentation has shown that a number of factors can be controlled that contribute to processing and delivery of a protein without denaturation. The protein may be prepared as a powder, with the powder particle size being chosen in light of the size of the ultimate organogel.

All organic solvents for the proteins may be chosen so that the proteins are not solvated by the organic solvents and are compatible with the protein. Another factor is oxygen, and elimination of oxygen is helpful in processing to avoid denaturation. Another factor is chemical reactions. These may be avoided by keeping the protein in a solid phase and free of solvents that dissolve the protein until such time as the protein is implanted.

One embodiment of particle preparation involves receiving a protein without substantial denaturation, e.g., from a supplier or animal or recombinant source. The protein is lyophilized, spray dried or concentrated or used as received. The protein is then prepared as a fine powder without denaturation by processing it in a solid state and avoiding high temperatures, moisture, and optionally in an oxygen free environment. Powders may be prepared by, for example, grinding, ball milling, or mortar-and-pestle a solid protein.

Making a protein agent or other water soluble biologic agent into a particle can be a useful first step for delivery of the agent from a solid phase. It is not, however, a sufficient step for achieving a well-controlled release from a matrix, or effective release over an extended period of time. Upon implantation, however, the particle will tend to be quickly dissolved as water contacts the particle and solvates the agents. In the case of a particle in a hydrogel, for instance, water permeates the hydrogel and contacts the particles. Unexpectedly, however, it is possible to prevent the water soluble biologic agents in the particles in the hydrogel from dissolving. Some mechanisms for doing so are set forth herein but are not to be used to limit the inventions to particular theories of action. One mechanism is apparently related to using a matrix that prevents the agents from moving away from the particle. And, even if a molecule of the agent dissolves, it is kept at the local site and will saturate the local site to prevent further solvation of other agent molecules. Another mechanism relates to the solvation of the matrix, which competes for water with the agents that are potentially soluble, with the matrix having a volume exclusion effect for interfering with agent solvation.

These mechanisms relate to achieving a spacing between molecular strands of the matrix that is dense. The crosslinking density of the organogel matrix (and thus the xerogel and the hydrogel matrix) is controlled by the overall molecular weight of the precursor(s) used as crosslinker(s) and other precursor(s) and the number of functional groups available per precursor molecule. A lower molecular weight between crosslinks such as 500 will give much higher crosslinking density as compared to a higher molecular weight between crosslinks such as 10,000. The crosslinking density also may be controlled by the overall percent solids of the crosslinker and functional polymer solutions. Yet another method to control crosslink density is by adjusting the stoichiometry of nucleophilic functional groups to electrophilic functional groups. A one to one ratio leads to the highest crosslink density. Precursors with longer distances between crosslinkable sites form gels that are generally softer, more compliant, and more elastic. Thus an increased length of a water-soluble segment, such as a polyethylene glycol, tends to enhance elasticity to produce desirable physical properties. Thus certain embodiments are directed to precursors with water soluble segments having molecular weights in the range of 2,000 to 100,000; artisans will immediately appreciate that all the ranges and values within the explicitly stated ranges are contemplated, e.g. 10,000 to 35,000. The solids content of the hydrogel can affect its mechanical properties and biocompatibility and reflects a balance between competing requirements. A relatively low solids content is useful, e.g., between about 2.5% to about 20%, including all ranges and values there between, e.g., about 2.5% to about 10%, about 5% to about 15%, or less than about 15%. Artisans will appreciate that the same materials may be used to make matrices with a great range of structures that will have highly distinct mechanical properties and performance, such that the achievement of a particular property should not be merely assumed based on the general types of precursors that are involved.

Delivery of Water Soluble Biologics and Other Therapeutic Agents

Various water soluble biologics and/or other therapeutic agents may be delivered with the systems described herein. The xerogel particles containing protein powders may be used to deliver a water soluble biologic and/or other therapeutic agent. The particles may be administered inside a xerogel. The xerogel may be a preformed structure, e.g., having at least 2 $cm^3$ of volume (artisans will immediately appreciate that all the ranges and values within the explicitly stated ranges are contemplated, e.g., about 2 to about 20 $cm^3$) or be a collection of particles. Alternatively, the xerogel particles may be administered directly, or in a pharmaceutically acceptable binder or carrier. Other materials may comprise the xerogel particles. Water soluble agents are one category of agents that may be delivered as powders within the xerogel. Other drugs may also be mixed into the xerogels, or with the xerogels, such as hydrophobic agents or small molecule drugs (water soluble or hydrophobic).

Proteins are a category of water soluble agents. The xerogel particles may be processed so that the proteins are incorporated and released without substantial denaturation and/or in their native conformation. Some anti-vascular endothelial growth factor (anti-VEGF) agents are therapeutic agent proteins. Anti-VEGF therapies are important in the treatment of certain cancers and in age-related macular degeneration. They can involve monoclonal antibodies such as bevacizumab (AVASTIN), antibody derivatives such as ranibizumab (LUCENTIS), or small molecules that inhibit the tyrosine kinases stimulated by VEGF: lapatinib (TYKERB), sunitinib (SUTENT), sorafenib (NEXAVAR), axitinib, and pazopanib. (Some of these therapies target VEGF receptors as opposed to the VEGFs.)

Some conventional ocular drug delivery systems deliver drugs with topical eye drops. For example, after cataract and vitreoretinal surgery, antibiotics are administered dropwise every few hours for several days. In addition, other drugs such as non-steroidal anti-inflammatory drugs (NSAIDS) may also need to be given frequently. Some of these eye drops, for example RESTASIS (Allergan), also have a stinging and burning sensation associated with their administration. RESTASIS is indicated for dry eye and has to be used by the patient several times a day. Similarly treatments for other ophthalmic diseases such as cystoid macular edema, diabetic macular edema (DME), and diabetic retinopathy also need administration of steroidal or NSAID drugs. Several vascular proliferative diseases such as macular degeneration are treated using intravitreal injections of VEGF inhibitors. These include drugs such as LUCENTIS and AVASTIN (Genentech) and MACUGEN (OSI). Such drugs may be delivered using the hydrogel-and-particle systems described herein, with the steps of repeated dosings being avoided; e.g., not making new applications of the drug daily, weekly, or monthly, or not using topical eye drops to administer the drug.

Various drug delivery systems are known. These various other systems generally include intravitreal implant reservoir type systems, biodegradable depot systems, or implants that need to be removed (non-erodeable). The state of the art in this regard has been delineated in texts such as "Intraocular Drug Delivery" (Jaffe et al., Taylor & Francis pub., 2006). However, most of these implants either need to be removed at term, can detach from their target site, may cause visual disturbances in the back of the eye or can be inflammatory themselves because of the liberation of a substantial amount of acidic degradation products. These implants are thus made to be very small with a very high drug concentration. Even though they are small, they still need to be deployed with needles over 25G (25 gauge) in size, or a surgical approach delivery system for implantation or removal as needed. In general, these are localized injections of drug solutions into the vitreous humor or intravitreal implants that use a biodegradable-approach or a removable-reservoir approach. For instance, localized injections delivered into the vitreous humor include anti-VEGF agents LUCENTIS or AVASTIN. POSURDEX (Allergan) is a biodegradable implant with indications for use being diabetic macular edema (DME) or retinal vein occlusions, with a 22 gauge injector delivery system used for delivery into the vitreous cavity; these are powerful drugs in a short drug delivery duration setting. The therapeutic agent is dexamethasone with polylactic/polyglycolic polymer matrix. Trials with POSURDEX for diabetic retinopathy are in progress. And for instance, a MEDIDURE implant (PSIVIDA) is used for DME indications. This implant's the therapeutic agent is fluocinolone acetonide, and has a nominal delivery life of 18 months or 36 months (two versions). An intravitreal, removable implant containing triamcinolone acetonide is being tested. Its nominal delivery life is about two years and requires surgical implantation. Its indication is for DME.

In contrast to these conventional systems, these or other therapeutic agents may be delivered using a collection of xerogel particles or systems comprising the particles. The xerogel particles comprise the agent. The xerogels, upon exposure to physiological fluids, imbibe the fluids to form hydrogels that are biocompatible for the eye, which is an environment that is distinctly different from other environments. The use of minimally inflammatory materials avoids angiogenesis, which is harmful in the eye in many situations. Biocompatible ocular materials thus avoid unintended angiogenesis; in some aspects, avoiding acidic degradation products achieves this goal. Further, by using hydrogels and hydrophilic materials (components having a solubility in water of at least one gram per liter, e.g., polyethylene glycols/oxides), the influx of inflammatory cells is also minimized; this process is in contrast to conventional use of non-hydrogel or rigid, reservoir-based ocular implants. Moreover, certain proteins may be avoided to enhance biocompatibility; collagen or fibrin glues, for instance, tend to promote inflammation or unwanted cellular reactions since these releases signals as they are degraded that promote biological activity. Instead, synthetic materials are used, or peptidic sequences not normally found in nature. Additionally, biodegradable materials may be used so as to avoid a chronic foreign body reaction, e.g., as with thermally-formed gels that do not degrade. Further, soft materials or materials made in situ to conform the shape of the surrounding tissues can minimize ocular distortion, and low-swelling materials may be used to eliminate vision-distortion caused by swelling. High or low pH materials may be avoided, both in the formation, introduction, or degradation phases.

The xerogels may be prepared with and used to deliver classes of drugs (and drugs to other parts of the body for local as well as systemic delivery) including steroids, non-steroidal anti-inflammatory drugs (NSAIDS), anti-cancer drugs, antibiotics, or others. The xerogels may be used to deliver drugs and therapeutic agents, e.g., an anti-inflammatory (e.g., Diclofenac), a pain reliever (e.g., Bupivacaine), a Calcium channel blocker (e.g., Nifedipine), an Antibiotic (e.g., Ciprofloxacin), a Cell cycle inhibitor (e.g., Simvastatin), a protein (e.g., Insulin). The particles may be used to deliver classes of drugs including steroids, NSAIDS, antibiotics, pain relievers, inhibitors of vascular endothelial growth factor (VEGF), chemotherapeutics, anti-viral drugs, for instance. Examples of NSAIDS are Ibuprofen, Meclofenamate sodium, mefanamic acid, salsalate, sulindac, tolmetin sodium, ketoprofen, diflunisal, piroxicam, naproxen, etodolac, flurbiprofen, fenoprofen calcium, Indomethacin, celoxib, ketrolac, and nepafenac. The drugs themselves may be small molecules, proteins, RNA fragments, proteins, glycosaminoglycans, carbohydrates, nucleic acid, inorganic and organic biologically active compounds where specific biologically active agents include but are not limited to: enzymes, antibiotics, antineoplastic agents, local anesthetics, hormones, angiogenic agents, anti-angiogenic agents, growth factors, antibodies, neurotransmitters, psychoactive drugs, anticancer drugs, chemotherapeutic drugs, drugs affecting reproductive organs, genes, and oligonucleotides, or other configurations.

A variety of drugs or other therapeutic agents may be delivered using these xerogel particles or other xerogel structures. A list of agents or families of drugs and examples of indications for the agents are provided. The agents may also be used as part of a method of treating the indicated condition or making a composition for treating the indicated condition. For example, AZOPT (a brinzolamide opthalmic suspension) may be used for treatment of elevated intraocular pressure in patients with ocular hypertension or open-angle glaucoma. BETADINE in a Povidone-iodine ophthalmic solution may be used for prepping of the periocular region and irrigation of the ocular surface. BETOPTIC (betaxolol HCl) may be used to lower intraocular pressure, or for chronic open-angle glaucoma and/or ocular hypertension. CILOXAN (Ciprofloxacin HCl opthalmic solution) may be used to treat infections caused by susceptible strains of microorganisms. NATACYN (Natamycin opthalmic suspension) may be used for treatment of fungal blepharitis, conjunctivitis, and keratitis. NEVANAC (Nepanfenac opthalmic suspension) may be used for treatment of pain and inflammation associated with cataract surgery. TRAVATAN (Travoprost ophthalmic solution) may be used for reduction of elevated intraocular pressure—open-angle glaucoma or ocular hypertension. FML FORTE (Fluorometholone ophthalmic suspension) may be used for treatment of corticosteroid-responsive inflammation of the palperbral and bulbar conjunctiva, cornea and anterior segment of the globe. LUMIGAN (Bimatoprost ophthalmic solution) may be used for reduction of elevated intraocular pressure-open-angle glaucoma or ocular hypertension. PRED FORTE (Prednisolone acetate) may be used for treatment of steroid-responsive inflammation of the palpebral and bulbar conjunctiva, cornea and anterior segment of the globe. PROPINE (Dipivefrin hydrochloride) may be used for control of intraocular pressure in chronic open-angle glaucoma. RESTASIS (Cyclosporine ophthalmic emulsion) may be used to increases tear production in patients, e.g., those with ocular inflammation associated with keratoconjunctivitis sicca. ALREX (Loteprednol etabonate ophthalmic suspension) may be used for temporary relief of seasonal allergic conjunctivitis. LOTEMAX (Loteprednol etabonate ophthalmic suspension) may be used for treatment of steroid-responsive inflammation of the palpebral and bulbar conjunctiva, cornea and anterior segment of the globe. MACUGEN (Pegaptanib sodium injection) may be used for Treatment of neovascular (wet) age-related macular degeneration. OPTIVAR (Azelastine hydrochloride) may be used for treatment of itching of the eye associated with allergic conjunctivitis. XALATAN (Latanoprost ophthalmic solution) may be used to reduce elevated intraocular pressure in patients, e.g., with open-angle glaucoma or ocular hypertension. BETIMOL (Timolol opthalmic solution) may be used for treatment of elevated intraocular pressure in patients with ocular hypertension or open-angle glaucoma. Latanoprost is the pro-drug of the free acid form, which is a prostanoid selective FP receptor agonist. Latanoprost reduces intraocular pressure in glaucoma patients with few side effects. Latanoprost has a relatively low solubility in aqueous solutions, but is readily soluble in organic solvents typically employed for fabrication of microspheres using solvent evaporation.

Further embodiments of agents for delivery include those that specifically bind a target peptide in vivo to prevent the interaction of the target peptide with its natural receptor or other ligands. AVASTIN, for instance, is an antibody that binds VEGF. And AFLIBERCEPT is a fusion protein that includes portions of a VEGF receptor to trap VEGF. An IL-1 trap that makes use of the extracellular domains of IL-1 receptors is also known; the trap blocks IL-1 from binding and activating receptors on the surface of cells. Embodiments of agents for delivery include nucleic acids, e.g., aptamers. Pegaptanib (MACUGEN), for example, is a pegylated anti-VEGF aptamer. An advantage of the particle-and-hydrogel delivery process is that the aptamers are protected from the in vivo environment until they are released. Further embodiments of agents for delivery include macromolecular drugs, a term that refers to drugs that are significantly larger than classical small molecule drugs, i.e., drugs such as oligonucleotides (aptamers, antisense, RNAi), ribozymes, gene therapy nucleic acids, recombinant peptides, and antibodies.

One embodiment comprises extended release of a medication for allergic conjunctivitis. For instance, ketotifen, an antihistamine and mast cell stabilizer, may be provided in particles and released to the eye as described herein in effective amounts to treat allergic conjunctivitis. Seasonal Allergic Conjunctivitis (SAC) and Perennial Allergic Conjunctivitis (PAC) are allergic conjunctival disorders. Symptoms include itching and pink to reddish eyes. These two eye conditions are mediated by mast cells. Non-specific measures to ameliorate symptoms conventionally include: cold compresses, eyewashes with tear substitutes, and avoidance of allergens. Treatment conventionally consists of antihistamine mast cell stabilizers, dual mechanism anti-allergen agents, or topical antihistamines. Corticosteroids might be effective but, because of side effects, are reserved for more severe forms of allergic conjunctivitis such as vernal keratoconjunctivitis (VKC) and atopic keratoconjunctivitis (AKC).

Moxifloxacin is the active ingredient in VIGAMOX, which is a fluoroquinolone approved for use to treat or prevent ophthalmic bacterial infections. Dosage is typically one-drop of a 0.5% solution that is administered 3 times a day for a period of one-week or more.

VKC and AKC are chronic allergic diseases where eosinophils, conjunctival fibroblasts, epithelial cells, mast cells, and/or TH2 lymphocytes aggravate the biochemistry and histology of the conjunctiva. VKC and AKC can be treated by medications used to combat allergic conjunctivitis.

Permeation agents are agents and may also be included in a gel, hydrogel, organogel, xerogel, and biomaterials as described herein. These are agents that assist in permeation of a drug into an intended tissue. Permeation agents may be chosen as needed for the tissue, e.g., permeation agents for skin, permeation agents for an eardrum, and permeation agents for an eye.

Xerogel Particle Blending and Collections

A collection of particles (powder particles of an agent and/or xerogel/hydrogel particles) may include sets of particles. The term xerogel/hydrogel refers to xerogels and/or the xerogels-hydrated-as-hydrogels. For instance, a collection may include some xerogel particles that contain a radioopaque agent, with those particles forming a set within the collection. Other sets are directed to particle sizes, with the sets having distinct shapes or size distributions. As discussed, particles can be made with well-controlled sizes and can thus be made and divided into various sets for combination into a collection.

Some sets are made of particles (xerogel/hydrogel) with a particular degradability. One embodiment involves a plurality of sets each having a distinct degradability profile. The different degradation rates provide different release profiles. Combinations of the different sets of particles may be made to achieve a desired profile, as demonstrated in FIGS. 6 and 7, referring to Example 2. Degradation times include 3 to 1000 days; artisans will immediately appreciate that all the ranges and values within the explicitly stated ranges are contemplated. For instance, a first set may have a median degradation time of from about 5 to about 8 days, a second set a median time of from about 30 to about 90 days, and a third set a median time of from about 180 to about 360 days.

Xerogel/hydrogel particles may be blended to achieve a desired protein release profile. Gels with different degradation rates (as hydrogels) can be combined to provide constant or near constant release that compensates for the inherently non-linear release profile of single gels.

A collection of xerogel/hydrogel particles may include sets of agents. For instance, some particles may be made to contain a first therapeutic agent, with those particles forming a set within the collection. And other sets may have another agent. Examples of agents are water soluble biologics, proteins, peptides, nucleic acids, small molecule drugs, and hydrophobic agents. Other sets may be directed to particle sizes, with the sets having distinct shapes or size distributions. As discussed, particles can be made with well-controlled sizes and divided into various sets for combination into a collection. These various sets may be freely mixed-and-matched in combinations and subcombinations, for example: sizes, degradability, therapeutic agents, and visualization agents.

Xerogel/hydrogels may further comprise agents that are not in a powder form. The agents may be disposed with the xerogel/hydrogel or mixed with the solution of other vehicle that is used with the xerogel/hydrogel. For example, a collection of xerogel particles may be hydrated at point of use to form a hydrogel by adding water or saline that further comprises a drug solution. Such drugs or agents may be the same as the agent that is in a powder in the xerogel/hydrogel so as to provide an initial burst of release, or may be for secondary therapy or visualization.

Lubricity

Collections may be made with sizes and lubricity for manual injection through a small gauge needle. Hydrophilic hydrogels crushed into spheroidal particles about 40 to about 100 microns diameter are small enough to be manually injected through a 30 gauge needle. Hydrophilic hydrogel particles were observed to pass with difficulty through small gauge needles/catheters, as reported in U.S. Publication No. 2011/0142936, which is hereby incorporated herein for all purposes; in case of conflict, the instant specification is controlling. The particle size contributes to resistance, as well as the viscosity of the solution. The particles tended to plug the needle. The resistance force is proportional to the viscosity of the fluid, with a more viscous fluid requiring more force to push through a small opening.

As reported in U.S. Publication No. 2011/0142936, it was unexpectedly found that increasing the viscosity of the solvent for the particles could lower the resistance to passage through a catheter and/or needle. This decrease may be attributed to using a solvent with a high osmolarity. Without being bound to a particular theory, the addition of these agents to improve injectability was caused by particle shrinkage, increased free water between particles which decreased particle-to-particle contributions to viscosity, and increased viscosity of the free water, which helped to pull the particles into and out of the syringes, preventing straining and plugging. The use of a linear polymer may further contribute thixotropic properties that are useful to prevent settling and encourage movement of the particles together with the solvent, but exhibit shear thinning when being forced out of a small opening. This approach was also observed to solve another problem, namely, a difficulty in moving particles from a solution through a needle/catheter since the particles tended to settle and otherwise elude pick-up. Expulsion through small bore openings of solutions of particles in aqueous solvent were observed; the solvent tended to move preferentially out of the applicator, leaving an excess of particles behind that could not be cleared from the applicator, or that plugged it, or in some instances could be cleared but only by use of an unsuitably large force not suited to an average user operating a hand-held syringe. The addition of osmotic agents, however, contributed viscosity and/or thixotropic behavior that helped to empty particles from an applicator.

Embodiments of the invention include the addition of an osmotic agent to a plurality of xerogel/hydrogel particles. Examples of such agents include salts and polymers. Embodiments include polymers, linear polymers, and hydrophilic polymers, or combinations of the same. Embodiments include polymers of between about 500 and about 100,000 molecular weight; artisans will immediately appreciate that all the ranges and values within the explicitly stated ranges are contemplated, e.g., about 5000 to about 50,000 molecular weight. Embodiments include, for example, a concentration of about 1% to about 50% w/w osmotic agent; artisans will immediately appreciate that all the ranges and values within the explicitly stated ranges are contemplated, e.g., 10% to 30%. The agent and hydrogel may be introduced into a patient and may be part of a kit for the same.

Precursors

Matrices may be prepared and used to contain the particles of water soluble biologics. Accordingly, embodiments are provided herein for making implantable matrices. Such matrices include matrices with a porosity of more than about 20% v/v; artisans will immediately appreciate that all the ranges and values within the explicitly stated range is contemplated. Precursors may be dissolved in an organic solvent to make an organogel. An organogel is a non-crystalline, non-glassy solid material composed of a liquid organic phase entrapped in a three-dimensionally cross-linked network. The liquid can be, for example, an organic solvent, mineral oil, or vegetable oil. The solubility and dimensions of the solvent are important characteristics for the elastic properties and firmness of the organogel. Alternatively, the precursor molecules may themselves be capable of forming their own organic matrix, eliminating the need for a tertiary organic solvent. The term precursor refers to a component that becomes part of the crosslinked matrix. A polymer that becomes crosslinked into the matrix is a precursor while a salt or a protein that is merely present in the matrix is not a precursor.

Removal of the solvent (if used) from the organogel provides a xerogel, a dried gel. The xerogels formed by, for example, freeze drying, may have a high porosity (at least about 20%, a large surface area, and a small pore size. Xerogels made with hydrophilic materials form hydrogels when exposed to aqueous solutions. High porosity xerogels hydrate more quickly than more dense xerogels. Hydrogels are materials that do not dissolve in water and retain a significant fraction (more than 20%) of water within their structure. In fact, water contents in excess of 90% are often known. Hydrogels may be formed by crosslinking water soluble molecules to form networks of essentially infinite molecular weight. Hydrogels with high water contents are typically soft, pliable materials. Hydrogels and drug delivery systems as described in U.S. Publication Nos. 2009/0017097, 2011/0142936 and 2012/0071865 may be adapted for use with the materials and methods herein by following the guidance provided herein; these references are hereby incorporated herein by reference for all purposes, and in case of conflict, the instant specification is controlling.

Organogels and hydrogels may be formed from natural, synthetic, or biosynthetic polymers. Natural polymers may include glycosminoglycans, polysaccharides, and proteins. Some examples of glycosaminoglycans include dermatan sulfate, hyaluronic acid, the chondroitin sulfates, chitin, heparin, keratan sulfate, keratosulfate, and derivatives thereof. In general, the glycosaminoglycans are extracted from a natural source and purified and derivatized. However, they also may be synthetically produced or synthesized by modified microorganisms such as bacteria. These materials may be modified synthetically from a naturally soluble state to a partially soluble or water swellable or hydrogel state. This modification may be accomplished by various well-known techniques, such as by conjugation or replacement of ionizable or hydrogen bondable functional groups such as carboxyl and/or hydroxyl or amine groups with other more hydrophobic groups.

For example, carboxyl groups on hyaluronic acid may be esterified by alcohols to decrease the solubility of the hyaluronic acid. Such processes are used by various manufacturers of hyaluronic acid products (such as Genzyme Corp., Cambridge, Mass.) to create hyaluronic acid based sheets, fibers, and fabrics that form hydrogels. Other natural polysaccharides, such as carboxymethyl cellulose or oxidized regenerated cellulose, natural gum, agar, agrose, sodium alginate, carrageenan, fucoidan, furcellaran, laminaran, hypnea, eucheuma, gum arabic, gum ghatti, gum karaya, gum tragacanth, locust beam gum, arbinoglactan, pectin, amylopectin, gelatin, hydrophilic colloids such as carboxymethyl cellulose gum or alginate gum crosslinked with a polyol such as propylene glycol, and the like, also form hydrogels upon contact with aqueous surroundings.

Synthetic organogels or hydrogels may be biostable or biodegradable. Examples of biostable hydrophilic polymeric materials are poly(hydroxyalkyl methacrylate), poly(electrolyte complexes), poly(vinylacetate) cross-linked with hydrolysable or otherwise degradable bonds, and water-swellable N-vinyl lactams. Other hydrogels include hydrophilic hydrogels known as CARBOPOL®, an acidic carboxy polymer (Carbomer resins are high molecular weight, allylpentaerythritol-crosslinked, acrylic acid-based polymers, modified with C10-C30 alkyl acrylates), polyacrylamides, polyacrylic acid, starch graft copolymers, acrylate polymer, ester cross-linked polyglucan. Such hydrogels are described, for example, in U.S. Pat. No. 3,640,741 to Etes, U.S. Pat. No. 3,865,108 to Hartop, U.S. Pat. No. 3,992,562 to Denzinger et al., U.S. Pat. No. 4,002,173 to Manning et al., U.S. Pat. No. 4,014,335 to Arnold and U.S. Pat. No. 4,207,893 to Michaels, all of which are incorporated herein by reference, with the present specification controlling in case of conflict.

Hydrogels and organogels may be made from precursors. The precursors are not the hydrogels/organogels but are crosslinked with each other to form the hydrogel/organogel. Crosslinks can be formed by covalent bonds or physical bonds. Examples of physical bonds are ionic bonds, hydrophobic association of precursor molecule segments, and crystallization of precursor molecule segments. The precursors can be triggered to react to form a crosslinked hydrogel. The precursors can be polymerizable and include crosslinkers that are often, but not always, polymerizable precursors. Polymerizable precursors are thus precursors that have functional groups that react with each other to form matrices and/or polymers made of repeating units. Precursors may be polymers.

Some precursors thus react by chain-growth polymerization, also referred to as addition polymerization, and involve the linking together of monomers incorporating double or triple chemical bonds. These unsaturated monomers have extra internal bonds which are able to break and link up with other monomers to form the repeating chain. Monomers are polymerizable molecules with at least one group that reacts with other groups to form a polymer. A macromonomer (or macromer) is a polymer or oligomer that has at least one reactive group, often at the end, which enables it to act as a monomer; each macromonomer molecule is attached to the polymer by reaction the reactive group. Thus macromonomers with two or more monomers or other functional groups tend to form covalent crosslinks. Addition polymerization is involved in the manufacture of, e.g., polypropylene or polyvinyl chloride. One type of addition polymerization is living polymerization.

Some precursors thus react by condensation polymerization that occurs when monomers bond together through condensation reactions. Typically these reactions can be achieved through reacting molecules incorporating alcohol, amine or carboxylic acid (or other carboxyl derivative) functional groups. When an amine reacts with a carboxylic acid an amide or peptide bond is formed, with the release of water. Some condensation reactions follow a nucleophilic acyl substitution, e.g., as in U.S. Pat. No. 6,958,212, which is hereby incorporated by reference herein in its entirety to the extent it does not contradict what is explicitly disclosed herein.

Some precursors react by a chain growth mechanism. Chain growth polymers are defined as polymers formed by the reaction of monomers or macromonomers with a reactive center. A reactive center is a particular location within a chemical compound that is the initiator of a reaction in which the chemical is involved. In chain-growth polymer chemistry, this is also the point of propagation for a growing chain. The reactive center is commonly radical, anionic, or cationic in nature, but can also take other forms. Chain growth systems include free radical polymerization, which involves a process of initiation, propagation and termination. Initiation is the creation of free radicals necessary for propagation, as created from radical initiators, e.g., organic peroxide molecules. Termination occurs when a radical reacts in a way that prevents further propagation. The most common method of termination is by coupling where two radical species react with each other forming a single molecule.

Some precursors react by a step growth mechanism, and are polymers formed by the stepwise reaction between functional groups of monomers. Most step growth polymers are also classified as condensation polymers, but not all step growth polymers release condensates.

Monomers may be polymers or small molecules. A polymer is a high molecular weight molecule formed by combining many smaller molecules (monomers) in a regular pattern. Oligomers are polymers having less than about 20 monomeric repeat units. A small molecule generally refers to a molecule that is less than about 2000 Daltons.

The precursors may thus be small molecules, such as acrylic acid or vinyl caprolactam, larger molecules containing polymerizable groups, such as acrylate-capped polyethylene glycol (PEG-diacrylate), or other polymers containing ethylenically-unsaturated groups, such as those of U.S. Pat. No. 4,938,763 to Dunn et al, U.S. Pat. Nos. 5,100,992 and 4,826,945 to Cohn et al, or U.S. Pat. Nos. 4,741,872 and 5,160,745 to DeLuca et al., each of which is hereby incorporated by reference herein in its entirety to the extent it does not contradict what is explicitly disclosed herein.

To form covalently crosslinked hydrogels, the precursors must be covalently crosslinked together. In general, polymeric precursors are polymers that will be joined to other polymeric precursors at two or more points, with each point being a linkage to the same or different polymers. Precursors with at least two reactive centers (for example, in free radical polymerization) can serve as crosslinkers since each reactive group can participate in the formation of a different growing polymer chain. In the case of functional groups without a reactive center, among others, crosslinking requires three or more such functional groups on at least one of the precursor types. For instance, many electrophilic-nucleophilic reactions consume the electrophilic and nucleophilic functional groups so that a third functional group is needed for the precursor to form a crosslink. Such precursors thus may have three or more functional groups and may be crosslinked by precursors with two or more functional groups. A crosslinked molecule may be crosslinked via an ionic or covalent bond, a physical force, or other attraction. A covalent crosslink, however, will typically offer stability and predictability in reactant product architecture.

In some embodiments, each precursor is multifunctional, meaning that it comprises two or more electrophilic or nucleophilic functional groups, such that a nucleophilic functional group on one precursor may react with an electrophilic functional group on another precursor to form a covalent bond. At least one of the precursors comprises more than two functional groups, so that, as a result of electrophilic-nucleophilic reactions, the precursors combine to form crosslinked polymeric products.

The precursors may have biologically inert and hydrophilic portions, e.g., a core. In the case of a branched polymer, a core refers to a contiguous portion of a molecule joined to arms that extend from the core, with the arms having a functional group, which is often at the terminus of the branch. A hydrophilic precursor or precursor portion has a solubility of at least 1 g/100 mL in an aqueous solution. A hydrophilic portion may be, for instance, a polyether, for example, polyalkylene oxides such as polyethylene glycol (PEG), polyethylene oxide (PEO), polyethylene oxide-co-polypropylene oxide (PPO), co-polyethylene oxide block or random copolymers, and polyvinyl alcohol (PVA), poly (vinyl pyrrolidinone) (PVP), poly (amino acids, dextran, or a protein. The precursors may have a polyalkylene glycol portion and may be polyethylene glycol based, with at least about 80% or 90% by weight of the polymer comprising polyethylene oxide repeats. The polyethers and more particularly poly (oxyalkylenes) or poly (ethylene glycol) or polyethylene glycol are generally hydrophilic. As is customary in these arts, the term PEG is used to refer to PEO with or without hydroxyl end groups.

A precursor may also be a macromolecule (or macromer), which is a molecule having a molecular weight in the range of a thousand to many millions. In some embodiments, however, at least one of the precursors is a small molecule of about 1000 Da or less. The macromolecule, when reacted in combination with a small molecule of about 1000 Da or less, is preferably at least five to fifty times greater in molecular weight than the small molecule and is preferably less than about 60,000 Da; artisans will immediately appreciate that all the ranges and values within the explicitly stated ranges are contemplated. A more preferred range is a macromolecule that is about seven to about thirty times greater in molecular weight than the crosslinker and a most preferred range is about ten to twenty times difference in weight. Further, a macromolecular molecular weight of 5,000 to 50,000 is useful, as is a molecular weight of 7,000 to 40,000 or a molecular weight of 10,000 to 20,000.

Certain macromeric precursors are the crosslinkable, biodegradable, water-soluble macromers described in U.S. Pat. No. 5,410,016 to Hubbell et al, which is hereby incorporated herein by reference in its entirety to the extent it does not contradict what is explicitly disclosed. These macromers are characterized by having at least two polymerizable groups, separated by at least one degradable region.

Synthetic precursors may be used. Synthetic refers to a molecule not found in nature or not normally found in a human. Some synthetic precursors are free of amino acids or free of amino acid sequences that occur in nature. Some synthetic precursors are polypeptides that are not found in nature or are not normally found in a human body, e.g., di-, tri-, or tetra-lysine. Some synthetic molecules have amino acid residues but only have one, two, or three that are contiguous, with the amino acids or clusters thereof being separated by non-natural polymers or groups. Polysaccharides or their derivatives are thus not synthetic.

Alternatively, natural proteins or polysaccharides may be adapted for use with these methods, e.g., collagens, fibrin (ogen)s, albumins, alginates, hyaluronic acid, and heparins. These natural molecules may further include chemical derivitization, e.g., synthetic polymer decorations. The natural molecule may be crosslinked via its native nucleophiles or after it is derivatized with functional groups, e.g., as in U.S. Pat. Nos. 5,304,595, 5,324,775, 6,371,975, and 7,129,210, each of which is hereby incorporated by reference to the extent it does not contradict what is explicitly disclosed herein. Natural refers to a molecule found in nature. Natural polymers, for example proteins or glycosaminoglycans, e.g., collagen, fibrinogen, albumin, and fibrin, may be crosslinked using reactive precursor species with electrophilic functional groups. Natural polymers normally found in the body are proteolytically degraded by proteases present in the body. Such polymers may be reacted via functional groups such as amines, thiols, or carboxyls on their amino acids or derivatized to have activatable functional groups. While natural polymers may be used in hydrogels, their time to gelation and ultimate mechanical properties must be controlled by appropriate introduction of additional functional groups and selection of suitable reaction conditions, e.g., pH.

Precursors may be made with a hydrophobic portion provided that the resultant hydrogel retains the requisite amount of water, e.g., at least about 20%. In some cases, the precursor is nonetheless soluble in water because it also has a hydrophilic portion. In other cases, the precursor makes dispersion in the water (a suspension) but is nonetheless reactable to from a crosslinked material. Some hydrophobic portions may include a plurality of alkyls, polypropylenes, alkyl chains, or other groups. Some precursors with hydrophobic portions are sold under the trade names PLURONIC F68, JEFFAMINE, or TECTRONIC. A hydrophobic molecule or a hydrophobic portion of a copolymer or the like is one that is sufficiently hydrophobic to cause the molecule (e.g., polymer or copolymer) to aggregate to form micelles or microphases involving the hydrophobic domains in an aqueous continuous phase or one that, when tested by itself, is sufficiently hydrophobic to precipitate from, or otherwise change phase while within, an aqueous solution of water at pH from about 7 to about 7.5 at temperatures from about 30 to about 50 degrees Centigrade.

Precursors may have, e.g., 2-100 arms, with each arm having a terminus, bearing in mind that some precursors may be dendrimers or other highly branched materials. An arm on a hydrogel precursor refers to a linear chain of chemical groups that connect a crosslinkable functional group to a polymer core. Some embodiments are precursors with between 3 and 300 arms; artisans will immediately appreciate that all the ranges and values within the explicitly stated ranges are contemplated, e.g., 4 to 16, 8 to 100, or at least 6 arms.

Thus hydrogels can be made, e.g., from a multi-armed precursor with a first set of functional groups and a low molecular-weight precursor having a second set of functional groups. For example, a six-armed or eight-armed precursor may have hydrophilic arms, e.g., polyethylene glycol, terminated with primary amines, with the molecular weight of the arms being about 1,000 to about 40,000; artisans will immediately appreciate that all ranges and values within the explicitly stated bounds are contemplated. Such precursors may be mixed with relatively smaller precursors, for example, molecules with a molecular weight of between about 100 and about 5000, or no more than about 800, 1000, 2000, or 5000 having at least about three functional groups, or between about 3 to about 16 functional groups; ordinary artisans will appreciate that all ranges and values between these explicitly articulated values are contemplated. Such small molecules may be polymers or non-polymers and natural or synthetic.

Precursors that are not dendrimers may be used. Dendritic molecules are highly branched radially symmetrical polymers in which the atoms are arranged in many arms and subarms radiating out from a central core. Dendrimers are characterized by their degree of structural perfection as based on the evaluation of both symmetry and polydispersity and require particular chemical processes to synthesize. Accordingly, an artisan can readily distinguish dendrimer precursors from non-dendrimer precursors. Dendrimers have a shape that is typically dependent on the solubility of its component polymers in a given environment, and can change substantially according to the solvent or solutes around it, e.g., changes in temperature, pH, or ion content. Precursors may be dendrimers, e.g., as in U.S. Publication Nos. 2004/0086479 and 2004/0131582 and PCT Publication Nos. WO07005249, WO07001926 and WO06031358, or the U.S. counterparts thereof; dendrimers may also be useful as multifunctional precursors, e.g., as in U.S. Publication Nos. 2004/0131582 and 2004/0086479 and PCT Publication Nos. WO06031388 and WO06031388; each of which US and PCT applications are hereby incorporated by reference herein in its entirety to the extent they do not contradict what is explicitly disclosed herein. Dendrimers are highly ordered possess high surface area to volume ratios, and exhibit numerous end groups for potential functionalization. Embodiments include multifunctional precursors that are not dendrimers.

Some embodiments include a precursor that consists essentially of an oligopeptide sequence of no more than five residues, e.g., amino acids comprising at least one amine, thiol, carboxyl, or hydroxyl side chain. A residue is an amino acid, either as occurring in nature or derivatized thereof. The backbone of such an oligopeptide may be natural or synthetic. In some embodiments, peptides of two or more amino acids are combined with a synthetic backbone to make a precursor; certain embodiments of such precursors have a molecular weight in the range of about 100 to about 10,000 or about 300 to about 500 Artisans will immediately appreciate that all ranges and values between these explicitly articulated bounds are contemplated.

Precursors may be prepared to be free of amino acid sequences cleavable by enzymes present at the site of introduction, including free of sequences susceptible to attach by metalloproteinases and/or collagenases. Further, precursors may be made to be free of all amino acids, or free of amino acid sequences of more than about 50, 30, 20, 10, 9, 8, 7, 6, 5, 4, 3, 2, or 1 amino acids. Precursors may be non-proteins, meaning that they are not a naturally occurring protein and cannot be made by cleaving a naturally occurring protein and cannot be made by adding synthetic materials to a protein. Precursors may be non-collagen, non-fibrin, non-fibrinogen, and non-albumin, meaning that they are not one of these proteins and are not chemical derivatives of one of these proteins. The use of non-protein precursors and limited use of amino acid sequences can be helpful for avoiding immune reactions, avoiding unwanted cell recognition, and avoiding the hazards associated with using proteins derived from natural sources. Precursors can also be non-saccharides (free of saccharides) or essentially non-saccharides (free of more than about 5% saccharides by w/w of the precursor molecular weight. Thus a precursor may, for example, exclude hyaluronic acid, heparin, or gellan. Precursors can also be both non-proteins and non-saccharides.

Peptides may be used as precursors. In general, peptides with less than about 10 residues are preferred, although larger sequences (e.g., proteins) may be used. Artisans will immediately appreciate that every range and value within these explicit bounds is included, e.g., 1-10, 2-9, 3-10, 1, 2, 3, 4, 5, 6, or 7. Some amino acids have nucleophilic groups (e.g., primary amines or thiols) or groups that can be derivatized as needed to incorporate nucleophilic groups or electrophilic groups (e.g., carboxyls or hydroxyls). Polyamino acid polymers generated synthetically are normally considered to be synthetic if they are not found in nature and are engineered not to be identical to naturally occurring biomolecules.

Some organogels and hydrogels are made with a polyethylene glycol-containing precursor. Polyethylene glycol (PEG, also referred to as polyethylene oxide when occurring in a high molecular weight) refers to a polymer with a repeat group $(CH_2CH_2O)_n$, with n being at least 3. A polymeric precursor having a polyethylene glycol thus has at least three of these repeat groups connected to each other in a linear series. The polyethylene glycol content of a polymer or arm is calculated by adding up all of the polyethylene glycol groups on the polymer or arm, even if they are interrupted by other groups. Thus, an arm having at least 1000 MW polyethylene glycol has enough $CH_2CH_2O$ groups to total at least 1000 MW. As is customary terminology in these arts, a polyethylene glycol polymer does not necessarily refer to a molecule that terminates in a hydroxyl group. Molecular weights are abbreviated in thousands using the symbol k, e.g., with 15K meaning 15,000 molecular weight, i.e., 15,000 Daltons. SG refers to succinimidyl glutarate. SS refers to succinimidyl succinate. SAP refers to succinimidyl adipate. SAZ refers to succinimidyl azelate. SS, SG, SAP and SAZ are succinimidyl esters that have an ester group that degrades by hydrolysis in water. Hydrolytically degradable thus refers to a material that would spontaneously degrade in vitro in an excess of water without any enzymes or cells present to mediate the degradation. A time for degradation refers to effective disappearance of the material as judged by the naked eye. Trilysine (also abbreviated LLL) is a synthetic tripeptide. PEG and/or hydrogels, as well as compositions that comprise the same, may be provided in a form that is pharmaceutically acceptable, meaning that it is highly purified and free of contaminants, e.g., pyrogens.

Functional Groups

The precursors for covalent crosslinking have functional groups that react with each other to form the material, either outside a patient, or in situ. The functional groups generally have polymerizable groups for polymerization or react with each other in electrophile-nucleophile reactions or are configured to participate in other polymerization reactions. Various aspects of polymerization reactions are discussed in the precursors section herein.

Thus in some embodiments, precursors have a polymerizable group that is activated by photoinitiation or redox systems as used in the polymerization arts, e.g., or electrophilic functional groups that are carbodiimidazole, sulfonyl chloride, chlorocarbonates, n-hydroxysuccinimidyl ester, succinimidyl ester or sulfasuccinimidyl esters, or as in U.S. Pat. No. 5,410,016 or 6,149,931, each of which are hereby incorporated by reference herein in its entirety to the extent they do not contradict what is explicitly disclosed herein. The nucleophilic functional groups may be, for example, amine, hydroxyl, carboxyl, and thiol. Another class of electrophiles are acyls, e.g., as in U.S. Pat. No. 6,958,212, which describes, among other things, Michael addition schemes for reacting polymers.

Certain functional groups, such as alcohols or carboxylic acids, do not normally react with other functional groups, such as amines, under physiological conditions (e.g., pH 7.2-11.0, 37° C.). However, such functional groups can be made more reactive by using an activating group such as N-hydroxysuccinimide. Certain activating groups include carbonyldiimidazole, sulfonyl chloride, aryl halides, sulfosuccinimidyl esters, N-hydroxysuccinimidyl ester, succinimidyl ester, epoxide, aldehyde, maleimides, imidoesters and the like. The N-hydroxysuccinimide esters or N-hydroxysulfosuccinimide (NHS) groups are useful groups for crosslinking of proteins or amine-containing polymers, e.g., amino terminated polyethylene glycol. An advantage of an NHS-amine reaction is that the reaction kinetics are favorable, but the gelation rate may be adjusted through pH or concentration. The NHS-amine crosslinking reaction leads to formation of N-hydroxysuccinimide as a side product. Sulfonated or ethoxylated forms of N-hydroxysuccinimide have a relatively increased solubility in water and hence their rapid clearance from the body. An NHS-amine crosslinking reaction may be carried out in aqueous solutions and in the presence of buffers, e.g., phosphate buffer (pH 5.0-7.5), triethanolamine buffer (pH 7.5-9.0), or borate buffer (pH 9.0-12), or sodium bicarbonate buffer (pH 9.0-10.0). Aqueous solutions of NHS based crosslinkers and functional polymers preferably are made just before the crosslinking reaction due to reaction of NHS groups with water. The reaction rate of these groups may be delayed by keeping these solutions at lower pH (pH 4-7). Buffers may also be included in the hydrogels introduced into a body.

In some embodiments, each precursor comprises only nucleophilic or only electrophilic functional groups, so long as both nucleophilic and electrophilic precursors are used in the crosslinking reaction. Thus, for example, if a crosslinker has nucleophilic functional groups such as amines, the functional polymer may have electrophilic functional groups such as N-hydroxysuccinimides. On the other hand, if a crosslinker has electrophilic functional groups such as sulfosuccinimides, then the functional polymer may have nucleophilic functional groups such as amines or thiols. Thus, functional polymers such as proteins, poly(allyl amine), or amine-terminated di- or multifunctional poly(ethylene glycol) can be used.

One embodiment has reactive precursor species with 3 to 16 nucleophilic functional groups each and reactive precursor species with 2 to 12 electrophilic functional groups each; artisans will immediately appreciate that all the ranges and values within the explicitly stated ranges are contemplated.

The functional groups may be, e.g., electrophiles reactable with nucleophiles, groups reactable with specific nucleophiles, e.g., primary amines, groups that form amide bonds with materials in the biological fluids, groups that form amide bonds with carboxyls, activated-acid functional groups, or a combination of the same. The functional groups may be, e.g., a strong electrophilic functional group, meaning an electrophilic functional group that effectively forms a covalent bond with a primary amine in aqueous solution at pH 9.0 at room temperature and pressure and/or an electrophilic group that reacts by a of Michael-type reaction. The strong electrophile may be of a type that does not participate in a Michaels-type reaction or of a type that participates in a Michaels-type reaction.

A Michael-type reaction refers to the 1, 4 addition reaction of a nucleophile on a conjugate unsaturated system. The addition mechanism could be purely polar, or proceed through a radical-like intermediate state(s); Lewis acids or appropriately designed hydrogen bonding species can act as catalysts. The term conjugation can refer both to alternation of carbon-carbon, carbon-heteroatom or heteroatom-heteroatom multiple bonds with single bonds, or to the linking of a functional group to a macromolecule, such as a synthetic polymer or a protein. Michael-type reactions are discussed in detail in U.S. Pat. No. 6,958,212, which is hereby incorporated by reference herein in its entirety for all purposes to the extent it does not contradict what is explicitly disclosed herein.

Examples of strong electrophiles that do not participate in a Michaels-type reaction are: succinimides, succinimidyl esters, or NHS-esters. Examples of Michael-type electrophiles are acrylates, methacrylates, methylmethacrylates, and other unsaturated polymerizable groups.

Initiating Systems

Some precursors react using initiators. An initiator group is a chemical group capable of initiating a free radical polymerization reaction. For instance, it may be present as a separate component, or as a pendent group on a precursor. Initiator groups include thermal initiators, photoactivatable initiators, and oxidation-reduction (redox) systems. Long wave UV and visible light photoactivatable initiators include, for example, ethyl eosin groups, 2,2-dimethoxy-2-phenyl acetophenone groups, other acetophenone derivatives, thioxanthone groups, benzophenone groups, and camphorquinone groups. Examples of thermally reactive initiators include 4,4' azobis(4-cyanopentanoic acid) groups, and analogs of benzoyl peroxide groups. Several commercially available low temperature free radical initiators, such as V-044, available from Wako Chemicals USA, Inc., Richmond, Va., may be used to initiate free radical crosslinking reactions at body temperatures to form hydrogel coatings with the aforementioned monomers.

Metal ions may be used either as an oxidizer or a reductant in redox initiating systems. For example, ferrous ions may be used in combination with a peroxide or hyperoxide to initiate polymerization, or as parts of a polymerization system. In this case, the ferrous ions would serve as a reductant. Alternatively, metal ions may serve as an oxidant. For example, the ceric ion (4+ valence state of cerium) interacts with various organic groups, including carboxylic acids and urethanes, to remove an electron to the metal ion, and leave an initiating radical behind on the organic group. In such a system, the metal ion acts as an oxidizer. Potentially suitable metal ions for either role are any of the transition metal ions, lanthanides and actinides, which have at least two readily accessible oxidation states. Particularly useful metal ions have at least two states separated by only one difference in charge. Of these, the most commonly used are ferric/ferrous; cupric/cuprous; ceric/cerous; cobaltic/cobaltous; vanadate V vs. IV; permanganate; and manganic/manganous. Peroxygen containing compounds, such as peroxides and hydroperoxides, including hydrogen peroxide, t-butyl hydroperoxide, t-butyl peroxide, benzoyl peroxide, cumyl peroxide may be used.

An example of an initiating system is the combination of a peroxygen compound in one solution, and a reactive ion, such as a transition metal, in another. In this case, no external initiators of polymerization are needed and polymerization proceeds spontaneously and without application of external energy or use of an external energy source when two complementary reactive functional groups containing moieties interact at the application site.

Visualization Agents

A visualization agent may be used as a powder in a xerogel/hydrogel; it reflects or emits light at a wavelength detectable to a human eye so that a user applying the hydrogel could observe the object when it contains an effective amount of the agent. Agents that require a machine aid for imaging are referred to as imaging agents herein, and examples include: radioopaque contrast agents and ultrasound contrast agents.

Some biocompatible visualization agents are FD&C BLUE #1, FD&C BLUE #2, and methylene blue. These agents are preferably present in the final electrophilic-nucleophilic reactive precursor species mix at a concentration of more than 0.05 mg/ml and preferably in a concentration range of at least 0.1 to about 12 mg/ml, and more preferably in the range of 0.1 to 4.0 mg/ml, although greater concentrations may potentially be used, up to the limit of solubility of the visualization agent. Visualization agents may be covalently linked to the molecular network of the xerogel/hydrogel, thus preserving visualization after application to a patient until the hydrogel hydrolyzes to dissolution.

Visualization agents may be selected from among any of the various non-toxic colored substances suitable for use in medical implantable medical devices, such as FD&C BLUE dyes 3 and 6, eosin, methylene blue, indocyanine green, or colored dyes normally found in synthetic surgical sutures. Reactive visualization agents such as NHS-fluorescein can be used to incorporate the visualization agent into the molecular network of the xerogel/hydrogel. The visualization agent may be present with either reactive precursor species, e.g., a crosslinker or functional polymer solution. The preferred colored substance may or may not become chemically bound to the hydrogel. The visualization agent may be used in small quantities, e.g., 1% weight/volume, more preferably less than 0.01% weight/volume and most preferably less than 0.001% weight/volume concentration; artisans will immediately appreciate that all the ranges and values within the explicitly stated ranges are contemplated. The agent tends to mark the location of the particle and provides an indication of its presence and dissolution rate.

Biodegradation

The xerogel may be formed from the organogel so that, upon hydration in physiological solution, a hydrogel is formed that is water-degradable, as measurable by the hydrogel losing its mechanical strength and eventually dissipating in vitro in an excess of water by hydrolytic degradation of water-degradable groups. This test is predictive of hydrolytically-driven dissolution in vivo, a process that is in contrast to cell or protease-driven degradation. Significantly, however, polyanhydrides or other conventionally-used degradable materials that degrade to acidic components tend to cause inflammation in tissues. The hydrogels, however, may exclude such materials, and may be free of polyanhydrides, anhydride bonds, or precursors that degrade into acid or diacids. The term degradation by solvation in water, also referred to as dissolving in water, refers to a process of a matrix gradually going into solution in, which is a process that cannot take place for a covalently crosslinked material and materials insoluble in water.

For example, electrophilic groups such as SG (N-hydroxysuccinimidyl glutarate), SS (N-hydroxysuccinimidyl succinate), SC (N-hydroxysuccinimidyl carbonate), SAP (N-hydroxysuccinimidyl adipate) or SAZ (N-hydroxysuccinimidyl azelate) may be used and have esteric linkages that are hydrolytically labile. More linear hydrophobic linkages such as pimelate, suberate, azelate or sebacate linkages may also be used, with these linkages being less degradable than succinate, glutarate or adipate linkages. Branched, cyclic or other hydrophobic linkages may also be used. Polyethylene glycols and other precursors may be prepared with these groups. The crosslinked hydrogel degradation may proceed by the water-driven hydrolysis of the biodegradable segment when water-degradable materials are used. Polymers that include ester linkages may also be included to provide a desired degradation rate, with groups being added or subtracted near the esters to increase or decrease the rate of degradation. Thus it is possible to construct a hydrogel with a desired degradation profile, from a few days to many months, using a degradable segment. If polyglycolate is used as the biodegradable segment, for instance, a crosslinked polymer could be made to degrade in about 1 to about 30 days depending on the crosslinking density of the network. Similarly, a polycaprolactone based crosslinked network can be made to degrade in about 1 to about 8 months. The degradation time generally varies according to the type of degradable segment used, in the following order: polyglycolate<polylactate<polytrimethylene carbonate<polycaprolactone. Thus it is possible to construct a hydrogel with a desired degradation profile, from a few days to many months, using a degradable segment.

A biodegradable linkage in the organogel and/or xerogel and/or hydrogel and/or precursor may be water-degradable or enzymatically degradable. Illustrative water-degradable biodegradable linkages include polymers, copolymers and oligomers of glycolide, dl-lactide, 1-lactide, dioxanone, esters, carbonates, and trimethylene carbonate. Illustrative enzymatically biodegradable linkages include peptidic linkages cleavable by metalloproteinases and collagenases. Examples of biodegradable linkages include polymers and copolymers of poly(hydroxy acid)s, poly(orthocarbonate)s, poly(anhydride)s, poly(lactone)s, poly(aminoacid)s, poly(carbonate)s, and poly(phosphonate)s.

If it is desired that a biocompatible crosslinked matrix be biodegradable or absorbable, one or more precursors having biodegradable linkages present in between the functional groups may be used. The biodegradable linkage optionally also may serve as the water soluble core of one or more of the precursors used to make the matrix. For each approach, biodegradable linkages may be chosen such that the resulting biodegradable biocompatible crosslinked polymer will degrade or be absorbed in a desired period of time.

Matrix materials may be chosen so that degradation products are absorbed into the circulatory system and essentially cleared from the body via renal filtration. The matrix materials may be hydrogels in a physiological solution. One method is to choose precursors that are not broken down in the body, with linkages between the precursors being degraded to return the precursors or precursors with small changes caused by the covalent crosslinking process. This approach is in contrast to choosing biological matrix materials that are destroyed by enzymatic processes and/or materials cleared by macrophages, or that result in by-products that are effectively not water soluble. Materials that are cleared from the body by renal filtration can be labeled and detected in the urine using techniques known to artisans. While there might be at least a theoretical loss of some of these materials to other bodily systems, the normal fate of the material is a kidney clearance process. The term essentially cleared thus refers to materials that are normally cleared through the kidneys.

Administration

Administration of a xerogel may be performed directly into the site of interest. For example, a lenticule of xerogel may be applied to a cornea, or a film may be applied to a dermis or epidermis. Xerogel particles may be administered by inhalation. And powder-delivery systems may be used to directly inject xerogel powders into a tissue.

Administration of a xerogel may also involve hydration at about the time of use, or at the point of use. The xerogel is exposed to an aqueous solution, for instance a physiological saline, and allowed to imbibe water to form a hydrogel. The hydrogel is implanted, either directly, surgically, or by injection through a syringe or catheter.

Embodiments of the invention include administration at or near an eye. The structure of the mammalian eye can be divided into three main layers or tunics: the fibrous tunic, the vascular tunic, and the nervous tunic. The fibrous tunic, also known as the tunica fibrosa oculi, is the outer layer of the eyeball consisting of the cornea and sclera. The sclera is the supporting wall of the eye and gives the eye most of its white color. It is extends from the cornea (the clear front section of the eye) to the optic nerve at the back of the eye. The sclera is a fibrous, elastic and protective tissue, composed of tightly packed collagen fibrils, containing about 70% water.

Overlaying the fibrous tunic is the conjunctiva. The conjunctiva is a membrane that covers the sclera (white part of the eye) and lines the inside of the eyelids. It helps lubricate the eye by producing mucus and tears, although a smaller volume of tears than the lacrimal gland. The conjunctiva is typically divided into three parts: (a) Palpebral or tarsal conjunctivam which is the conjunctiva lining the eyelids; the palpebral conjunctiva is reflected at the superior fornix and the inferior fornix to become the bulbar conjunctiva, (b) Fornix conjunctiva: the conjunctiva where the inner part of the eyelids and the eyeball meet, (c) Bulbar or ocular conjunctiva: the conjunctiva covering the eyeball, over the sclera. This region of the conjunctiva is bound tightly and moves with the eyeball's movements. The conjunctiva effectively surrounds, covers, and adheres to the sclera. It is has cellular and connective tissue, is somewhat elastic, and can be removed, teased away, or otherwise taken down to expose a surface area of the sclera.

The vascular tunic, also known as the tunica vasculosa oculi, is the middle vascularized layer which includes the iris, ciliary body, and choroid. The choroid contains blood vessels that supply the retinal cells with oxygen and remove the waste products of respiration. The nervous tunic, also known as the tunica nervosa oculi, is the inner sensory which includes the retina. The retina contains the photosensitive rod and cone cells and associated neurons. The retina is a relatively smooth (but curved) layer. It does have two points at which it is different; the fovea and optic disc. The fovea is a dip in the retina directly opposite the lens, which is densely packed with cone cells. The fovea is part of the macula. The fovea is largely responsible for color vision in humans, and enables high acuity, which is necessary in reading. The optic disc is a point on the retina where the optic nerve pierces the retina to connect to the nerve cells on its inside.

The mammalian eye can also be divided into two main segments: the anterior segment and the posterior segment. The anterior segment consists of an anterior and posterior chamber. The anterior chamber is located in front of the iris and posterior to the corneal endothelium and includes the pupil, iris, ciliary body and aqueous fluid. The posterior chamber is located posterior to the iris and anterior to the vitreous face where the crystalline lens and zonules fibers are positioned between an anterior and posterior capsule in an aqueous environment.

The cornea and lens help to converge light rays to focus onto the retina. The lens, behind the iris, is a convex, springy disk which focuses light, through the second humour, onto the retina. It is attached to the ciliary body via a ring of suspensory ligaments known as the Zonule of Zinn. The ciliary muscle is relaxed to focus on an object far away, which stretches the fibers connecting it with the lens, thus flattening the lens. Light enters the eye, passes through the cornea, and into the first of two humors, the aqueous humour. Approximately two-thirds of the eye's total refractive power comes from the cornea which has a fixed curvature. The aqueous humor is a clear mass which connects the cornea with the lens of the eye, helps maintain the convex shape of the cornea (necessary to the convergence of light at the lens) and provides the corneal endothelium with nutrients.

The posterior segment is located posterior to the crystalline lens and in front of the retina. It represents approximately two-thirds of the eye that includes the anterior hyaloid membrane and all structures behind it: the vitreous humor, retina, c, and optic nerve. On the other side of the lens is the second humour, the vitreous humour, which is bounded on all sides: by the lens, ciliary body, suspensory ligaments and by the retina. It lets light through without refraction, helps maintain the shape of the eye and suspends the delicate lens.

Figure 8:
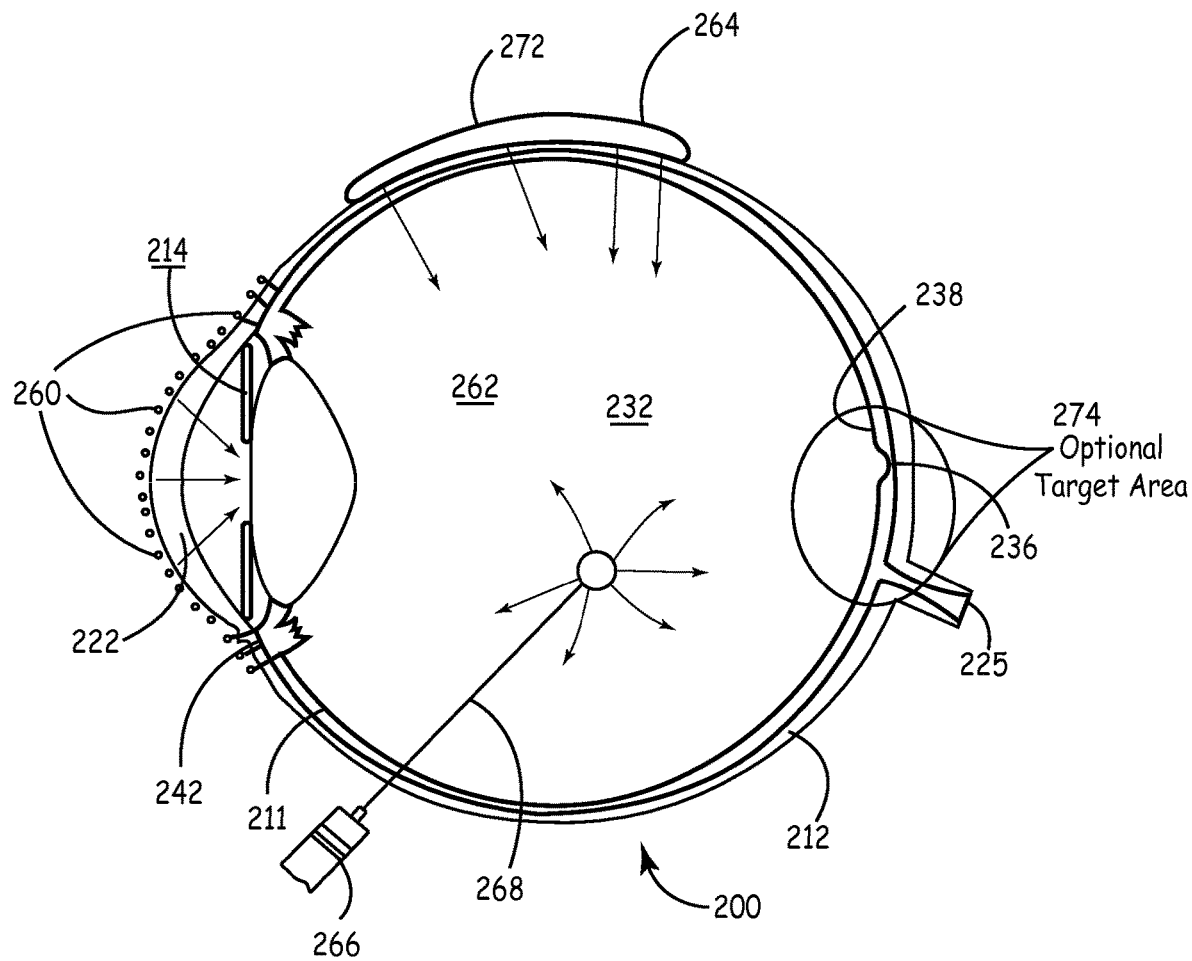
FIG. 8 is an illustration of various sites at or near an eye for application of a biomaterial.

FIG. 8 shows certain points of delivery at or near eye 200. Eye 200 includes sclera 212, iris 214, cornea 222, vitreous body 232, zonular spaces 242, fovea 236, retina 238, and optic nerve 225. One area for delivery is topically at 260, with area 260 being indicated by dots on surface of eye 200. Another area is intravitreally as indicated by numeral 262, or trans-sclerally, as indicated by numeral 264. In use, for example a syringe 266, catheter (not shown) or other device is used to deliver a xerogel (or gel or hydrogel or a precursors thereof), optionally through needle 268, into the eye, either intravitrealy, as at 262 or peri-ocularly, as at 272. Another area is subconjunctivally (not shown), below the conjunctiva 211 and above the sclera 212. Drugs or other therapeutic agents are released to the intra-ocular space. In the case of back-of-the-eye diseases, drugs may be targeted via the peri-ocular or intravitreal route to target approximate area 274, where they interact with biological features to achieve a therapy. An embodiment is placement of a xerogel in contact with retina 238 or near retina 238 without contacting it. For instance, xerogels, hydrogels and/or particles (or rods, microspheres, a single material, beads, or other shapes set forth herein) may be delivered to a location adjacent to, or upon, retina 238. The hydrogel advantageously is anchored in the vitreous gel and does not allow diffusion of the particles. In contrast, other systems that use a rod or slippery microspheres do not provide anchoring and diffusion or migration in response to movement of, or rubbing of, the eye. The placement of the depot at or near the retina (or other location) allows a high concentration to be achieved at the intended site, with small particles being usable to deliver the drugs for effective treatment. In contrast, spheres, rods, or other shapes that are too large to diffuse or migrate have a volume/surface area ration that is unfavorable for effective controlled release. Another area for placement of a xerogel, hydrogel and/or particles, or other materials comprising the particles is in a punctum (not shown), e.g., by placing particles in a punctal plug (silicone, polysaccharide, hydrogel, or other material) that is inserted into a punctum of an eye.

Sites where drug delivery depots may be formed in or near an eye include the anterior chamber, the vitreous (intravitreal placement), episcleral, in the posterior subtenon's space (inferior fornix), subconjunctival, on the surface of the cornea or the conjunctiva, among others. Periocular drug delivery of an ophthalmic hydrogel implant using subconjunctival, retrobulbar or sub-Tenon's placement has the potential to offer a safer and enhanced drug delivery system to the retina compared to topical and systemic routes.

Figure 9A:
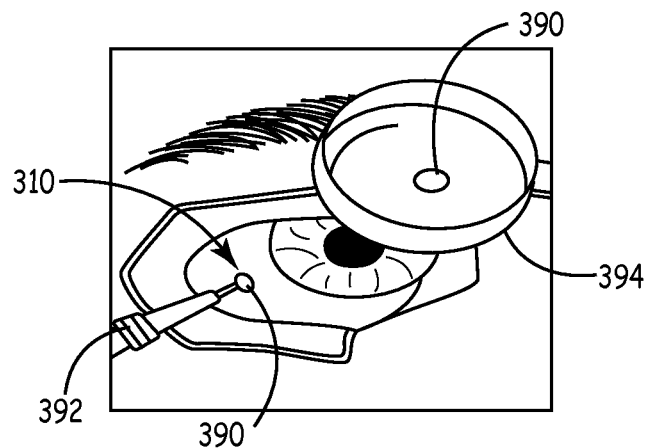
FIG. 9A is an illustration of a method for placing a biomaterial in an eye, and depicts a process of inserting a needle into an eye.
Figure 9B:
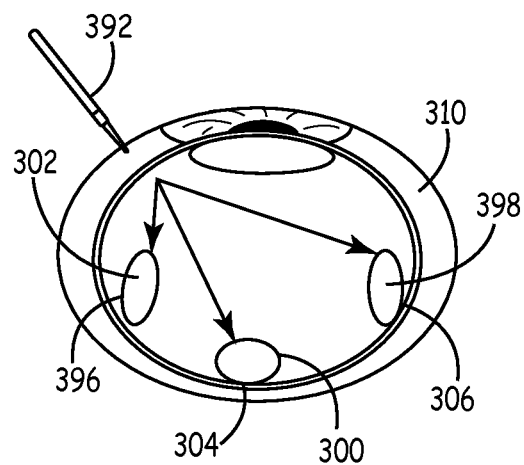
FIG. 9B depicts various examples of sites to receive the biomaterial in the eye of FIG. 9A.

An example of in situ placement is illustrated for an intravitreal implant in FIG. 9A. In FIG. 9A, a xerorogel implant is injected intravitrealy about 2.5 mm posterior to the limbus through a pars plana incision 390 using a sub-retinal cannula 392, as shown by depiction of magnifying glass 394 held so as to visualization incision 390 on eye 310, which may be made following dissecting-away or otherwise clearing the conjunctiva, as needed. A sub-retinal cannula 392 (or other appropriate cannulas) is then inserted through incision 390 and positioned intraocularly to the desired target site, e.g., at least one of sites 396, 398, 300 (FIG. 9B) where the xerogel(s) are introduced and subsequently form a hydrogel in situ. The xerogels form into an absorbable gel 302, 304, and/or 306, adhering to the desired target site. Particles comprising a therapeutic agent may be included in the gel or gels. Significantly, it is possible to use a fine gauge needle to place the precursors. Embodiments include placement with a 25 gauge needle. Further embodiments include using a needle smaller in diameter than 25 gauge, e.g., 26, 27, 30, 31, 32 gauge.

Intravitreal in situ implant embodiments can improve the efficacy and pharmacokinetics of potent therapeutic agents in the treatment of eye diseases and minimize patient side effects in several ways. First, the implant can be placed in the vitreous cavity at a specific disease site, bypassing the topical or systemic routes and thereby increasing drug bioavailability. Secondly, the implant maintains local therapeutic concentrations at the specific target tissue site over an extended period of time. Thirdly, the number of intravitreal injections would be substantially reduced over a 12 month therapy regimen, thereby reducing patient risk of infection, retinal detachment and transient visual acuity disturbances (white specks floating in the vitreous) that can occur until the drug in the vitreous migrates down toward the inferior wall of the eye and away from the portion of the central vitreous or macula.

The xerogels or the xerogels-hydrated-as-hydrogels (the xerogel/hydrogels) may be placed on scleral tissue either with or without the presence of the conjunctiva. The xerogel/hydrogels may be adhered to the sclera or other tissue near the sclera to promote drug diffusion through the intended tissue or to provide a stable depot to direct the therapeutic agents as required. A hydrogel adhesive such as RESURE® sealant may be employed as an adhesion aid. In some embodiments, the conjunctiva of the eye may be removed, macerated, dissected away, or teased-free so that the tissue can be lifted away from the sclera to access a specific region of the sclera for implantation or injection of the xerogel/hydrogels. A xerogel/hydrogel is placed to make a layer on, and adhere to, the surface. The conjunctiva may be allowed to contact the tissue if it is still present or retains adequate mechanical integrity to do so. In some embodiments the xerogel/hydrogels is comprised of at least 50%, 75%, 80%, 90%, or 99% w/w water-soluble precursors (calculated by measuring the weight of the hydrophilic precursors and dividing by the weight of all precursors, so that the weight of water or solvents or non-hydrogel components is ignored) to enhance the non-adhesive properties of the hydrogel. In some embodiments, such hydrophilic precursors substantially comprise PEOs. In some embodiments, drugs to reduce tissue adherence mediated by biological mechanisms including cell mitosis, cell migration, or macrophage migration or activation, are included, e.g., anti-inflammatories, anti-mitotics, antibiotics, PACLITAXEL, MITOMYCIN, or taxols.

In other embodiments, the sclera is not substantially cleared of the conjunctiva. The conjunctiva is a significant tissue mass that overlays much or all of the sclera. The conjunctiva may be punctured or penetrated with a needle or catheter or trocar and precursors introduced into a space between the sclera and conjunctiva. This placement of the implant is referred to as a subconjunctival location. In some cases the conjunctiva may be punctured to access a natural potential space between the tissues that is filled by the precursors. In other cases, a potential or actual space is created mechanically with a trocar, spreader, or the like, that breaks the adherence between the sclera and conjunctiva so that precursors may be introduced. The conjunctiva has enough elasticity to allow useful amounts of a xerogel to be introduced or forced into such natural or created spaces. Accordingly, in some cases, the xerogel/hydrogel volume is between about 0.25 to about 5 ml; artisans will immediately appreciate that all the ranges and values within the explicitly stated ranges are contemplated, e.g., about 1 ml or from 0.5 ml to about 1.5 ml.

Moreover, removal of a xerogel that has formed a hydrogel, whether present intraocularly or periocularly, is also readily achieved using either a vitrectomy cutter if the implant is located in the vitreous cavity or a manual I/A syringe and cannula if the implant is located on the scleral surface or irrigation/aspiration handpiece. This contrasts with major surgical procedures needed for the removal of some conventional non-absorbable implants.

In further embodiments, a xerogel/hydrogel material may be placed into the patient, e.g., in a tissue or organ, including subcutaneous, intramuscular, intraperitoneally, in a potential space of a body, or in a natural cavity or opening. The material provides a depot for release of an agent over time. Embodiments thus include between about 0.5 and about 500 ml volumes for placement (referring to total volume in the case of particle collections delivered); artisans will immediately appreciate that all the ranges and values within the explicitly stated ranges are contemplated, e.g., from 1 to 10 ml or from 5 to 50 ml. Intraperitoneal or intramuscular injection, for instance, is a useful area for extended control release of agents over hours, days, or weeks.

The materials described herein may be used to deliver drugs or other therapeutic agents (e.g., imaging agents or markers). One mode of application is to apply a mixture of xerogel/hydrogel particles and other materials (e.g., therapeutic agent, buffer, accelerator, initiator) through a needle, cannula, catheter, or hollow wire to a site. The mixture may be delivered, for instance, using a manually controlled syringe or mechanically controlled syringe, e.g., a syringe pump. Alternatively, a dual syringe or multiple-barreled syringe or multi-lumen system may be used to mix the xerogel/hydrogel particles at or near the site with a hydrating fluid and/or other agents.

The xerogels may be provided in flowable form to the site, e.g., as flowable particles. The xerogels may be suspended in a liquid and applied to the site. The xerogel particles may be made to have a maximum diameter for manual passage out of a syringe through a 3 to 5 French catheter, or a 10 to 30 gauge needle. Artisans will immediately appreciate that all the ranges and values within the explicitly stated ranges are contemplated, e.g., 25 to 30 gauge. The use of small needles is particular advantageous in the eye, which is a sensitive organ. Applications to other organs are also advantageous, e.g., to control bleeding or other damage. The particles may be formed by creating a hydrogel and then breaking it up into smaller pieces. The material may be, e.g., ground in a ball mill or with a mortar and pestle, or chopped or diced with knives or wires. Or the material may be cut-up in a blender. Another process involves forcing the material in the organogel or gel step through a mesh, collecting the fragments, and passing them through the same mesh or another mesh until a desired size is reached, followed by making the xerogel. The xerogel/hydrogel may contain the therapeutic agent-loaded particles. Some or all of the hydrogel particles may contain the therapeutic agent-loaded particles. In some embodiments, a first set of therapeutic agent-loaded particles loaded with a first therapeutic agent is included inside a first set of xerogel particles and a second set of therapeutic agent-loaded particles loaded with a second therapeutic agent is included inside a second set of xerogel particles. In this manner, a plurality of agents may be released from a single implant. Embodiments of the particles include those with a particular shape such as sphere, rod, or disc.

Embodiments include placement of a plurality of xerogel/hydrogel particles. The xerogel/hydrogel particles may comprise a therapeutic agent, e.g., a protein such as an anti-VEGF. The particles may be made with a sized for manual passage through a 27-gauge or smaller diameter needle. The pressure to force the particles through the needle may be provided manually.

An alternative to delivery of particles is to pre-form the gel as a shaped article and then introduce the material into the body. For example, the xerogel/hydrogels may be formed as spheres, rods, cylinders, or other shapes. Embodiments include solid rods of xerogel/hydrogels for subcutaneous implantation and delivery of one or more agents.

Xerogel/hydrogels as set forth herein may be used for tissue augmentation. The use of collagen as for dermal augmentation is well known. Xerogel/hydrogels, for example particulates, may be used for dermal filler or for tissue augmentation. Embodiments include injecting or otherwise placing a plurality of particles in a tissue, or forming a hydrogel in situ. The material may be injected or otherwise placed at the intended site.

Xerogel/hydrogels as set forth herein may be used to separate tissues to reduce a dose of radioactivity received by one of the tissues. As set forth in U.S. Pat. No. 7,744,913, which is hereby incorporated by reference herein for all purposes with the present specification controlling in case of conflict, spacer materials may be placed in a patient. Certain embodiments are a method comprising introducing a spacer to a position between a first tissue location and a second tissue location to increase a distance between the first tissue location and the second tissue location. Further, there may be a step of administering a dose of radioactivity to at least the first tissue location or the second tissue location. A method, for example, is delivering a therapeutic dose of radiation to a patient comprising introducing a biocompatible, biodegradable particulate xerogel, e.g., a collection of particles optionally with radioopaque contents, between a first tissue location and a second tissue location to increase a distance between the first tissue location and the second tissue location, and treating the second tissue location with the therapeutic dose of radiation so that the presence of the filler device causes the first tissue location to receive less of the dose of radioactivity compared to the amount of the dose of radioactivity the first tissue location would receive in the absence of the spacer. The spacer may be introduced as a xerogel that forms a hydrogel in the patient that is removed by biodegradation of the spacer-hydrogel in the patient. An example is the case wherein the first tissue location is associated with the rectum and the second tissue location is associated with the prostate gland. The amount of reduction in radiation can vary. Embodiments include at least about 10% to about 90%; artisans will immediately appreciate that all the ranges and values within the explicitly stated ranges are contemplated, e.g., at least about 50%. The radiation may alternatively be directed to a third tissue so that the first tissue or the second tissue received a lower amount of radiation as a result of its separation from the other tissue(s). The first tissue and the second tissue may be adjacent to each other in the body, or may be separate from each other by other tissues. Spacer volumes for separating tissues are dependent on the configuration of the tissues to be treated and the tissues to be separated from each other. In many cases, a volume of about 20 cubic centimeters (cc's or mls) is suitable. In other embodiments, as little as about 1 cc might be needed. Other volumes are in the range of about 5-1000 cc; artisans will immediately appreciate that all the ranges and values within the explicitly stated ranges are contemplated, e.g., 10-30 cc. In some embodiments, spacers are administered in two doses at different times so as to allow the tissues to stretch and accommodate the spacer and thereby receive a larger volumes of spacer than would otherwise be readily possible. Tissues to be separated by a spacer include, for example, at least one of a rectum, prostate, and breast, or a portion thereof. For instance, a first portion of a breast may be separated from a second portion.

Kits

Kits or systems for making hydrogels from a xerogel may be prepared so that the xerogels are stored in the kit and made into a hydrogel when needed for use with a patient. And kits may be made for applying a xerogel in a xerogel form. Applicators may be used in combination with the xerogel and/or hydrogel. The kits are manufactured using medically acceptable conditions and contain components that have sterility, purity and preparation that is pharmaceutically acceptable. The kit may contain an applicator as appropriate, as well as instructions. Xerogel particles comprising a therapeutic agent may be available for mixing with a solution that is in the kit or provided separately. The xerogel components may be provided as: one or more containers of a xerogel that form a hydrogel, with the xerogel being in the form of a plurality of particles that are placed into the patient, or as a unitary implant. Solvents/ solutions may be provided in the kit or separately, or the components may be pre-mixed with the solvent. The kit may include syringes and/or needles for mixing and/or delivery. The kit or system may comprise components set forth herein.

Some embodiments provide a single applicator, e.g., one syringe that comprises xerogel particles for delivery, with an aqueous solution being added to the applicator for hydration, followed by use of the syringe to place the materials in a patient. The xerogel particle solvent may be essentially water, meaning about 99% v/v of the solvent is water, with salts or buffers being present as desired. Other solvents may be used that are safe and biocompatible, e.g., dimethylsulfoxide. The xerogel particles may further comprise powders of proteins and/or other agents.

Packaging for a precursor and/or for an entire kit is preferably performed under dry conditions that are oxygen-free. The precursors and/or kit components may be placed in a hermetically sealed container that is not permeable to moisture or oxygen, for instance, glass or metal (foil) containers.

The xerogels containing the protein powder, or other solid phase, water soluble biologics, may be gamma sterilized at the end of the implantable material manufacturing process. Alternatively or furthermore there may be a sterilization process either before and/or after assembly and sealing of a kit. Low moisture conditions are often helpful in this technique. It has been observed that the solid phase dispersed powders resist the formation of aggregates and crosslinking under gamma radiation. This result is unexpected and surprising since gamma radiation sterilization is generally believed to harm protein or peptide biologics. Without being bound to a particular theory of operation, it is believed that the small particle size and absence of moisture disfavors these unwanted reactions.

Further Description (1) A first embodiment of the invention is directed to a process of making a medical material comprising forming an organogel around a powder of a water soluble biologic, with the powder being dispersed in the organogel. (2) A second embodiment of the invention is directed to a process of making a medical material comprising forming an gel around a powder of a water soluble biologic, with the powder being dispersed in the gel, wherein forming the gel comprises preparing a melt of one or more precursors and covalently crosslinking the precursors. (3) A third embodiment of the invention is directed to process of making a medical material comprising forming an organogel around particles of a powder of a biologic, with the particles being dispersed within the organogel, and removing solvents from the organogel, thereby forming a xerogel, said process being performed in an absence of water. (4) A fourth embodiment of the invention is directed to a process of making a medical material comprising forming an organogel or a gel from a melt, making a xerogel from the (organo)gel, and providing the xerogel as a collection of particles, wherein the xerogel is a hydrogel upon exposure to an aqueous solution. (5) A fifth embodiment of the invention is directed to a pharmaceutically acceptable material as in any of embodiment's I-IV. (6) A sixth embodiment of the invention is directed to a medical material comprising a pharmaceutically acceptable biodegradable xerogel comprising dispersed protein particles, the protein being a therapeutic agent and having a secondary and/or a tertiary structure. Further, said protein may be released from the particles in aqueous solution in a conformation that is substantially free of denaturation. (7) A seventh embodiment of the invention is directed to a (pharmaceutically acceptable) biomaterial for controlled release of a therapeutic water soluble biologic comprising a pharmaceutically acceptable xerogel that comprises solid particles of the biologic dispersed therein, (optionally, with the xerogel being free of hydrophobic materials) and with the xerogel being a hydrogel when exposed to water. (8) An eighth embodiment is a method of making any of the materials of embodiments VI or VII.

Further embodiments are: (9) as in any of 1-8 wherein the (water soluble) biologic is a protein (10) as in any of 1-9 wherein the protein has a molecular mass of at least about 10,000 Daltons and a sugar is associated with the protein (11) as in any of 1-10 wherein the powder is used and is a first powder, with the process further comprising a second powder that comprises a second water soluble biologic agent, with the first powder and the second powder being dispersed through the organogel (12) as in any of 1-11 wherein the powder is used and has an average particle size between about 1 µm and about 10 µm (13) as in any of 1-12 wherein the organogel is formed in an absence of aqueous solution (14) as in any of 1-13 comprising removing solvents from the organogel as may be needed to thereby form a xerogel (15) as in any of 1-14 comprising removing solvents by a process chosen from the group consisting of vacuum removal, lyophilization, and freezing followed by application of a vacuum (16) as in any of 1-15 comprising the xerogel, wherein the xerogel is a hydrogel upon exposure to an aqueous solution (17) as in any of 1-15 comprising the powder, wherein the (water soluble) biologics remain substantially in the powder, in a solid phase, when the hydrogel is formed, and slowly dissolve over a period of time when the hydrogel is exposed to physiological solution in vivo in a mammal (18) as in 17 with said dissolving being in a period of time is in a range from about 1 week to about 52 weeks (19) as in any of 1-18 wherein the biologic in the gel is a protein having a secondary and/or a tertiary structure, with the protein being released in a conformation that is substantially free of denaturation as measurable by, for example, enzyme-linked immunosorbent assay and isoelectric focusing (20) as in any of 1-19 wherein the gel or organogel or xerogel comprises covalently crosslinked hydrophilic polymers (21) as in any of 1-20 wherein the gel organogel or xerogel organogel comprises covalently crosslinked hydrophilic polymers chosen from the group consisting of polyethylene oxide, polyvinyl pyrrolidinone, hyaluronic acid, polyhydroxyethlymethacrylate, and block copolymers thereof (22) as in any of 1-21 wherein, when the hydrogel is present, the hydrogel is biodegradable by spontaneous hydrolysis of hydrolytically degradable linkages chosen from the group consisting of esters, carbonates, anhydrides and orthocarbonates (23) as in any of 1-22 wherein, when the organogel is present, the organogel comprises block copolymers that form the organogel and that, after the solvents are removed to form a xerogel, form a hydrogel upon exposure to an aqueous solution (24) as in any of 1-23 wherein, when the organogel is present, the organogel comprises wherein the organogel (and the hydrogel) comprises ionically crosslinked polymers (25) as in any of 1-24 wherein, when the organogel is present, the organogel comprises a member chosen from the group consisting of alginate, gellan, collagen, and polysaccharide (25) as in any of 1-24 comprising forming a plurality of particles out of: (a) the gel (b) the organogel (c) a xerogel made from the gel or the organogel, or (d) a hydrogel made from the gel or organogel (26) as in any of 1-25 wherein, when the organogel is present, forming the organogel from a precursor in an organic solvent, with the precursor being chemically reacted to form covalent bonds to thereby form the organogel, wherein the organogel is covalently crosslinked (27) as in any of 1-26 wherein the precursor is reacted by free radical polymerization to form the organogel (28) as in any of 1-27 wherein the precursor is a first precursor comprising a first functional group and further comprising a second precursor comprising a second functional group, with the first functional group and the second functional group being reactive in the organic solvent to form the covalent bonds (29) as in 28 wherein the first functional group and the second functional group are each chosen from the group consisting of electrophile and nucleophile, and the reaction between the first functional group and second functional group is an electrophilic-nucleophilic reaction that forms the covalent bond (30) as in 28 or 29 wherein the electrophilic group comprises succimide, succinimide ester, n-hydroxysuccinimide, maleimide, succinate, nitrophenyl carbonate, aldehyde, vinylsulfone, azide, hydrazide, isocyanate, diisocyanate, tosyl, tresyl, or carbonyldiimidazole (31) as in any of 28-30 wherein the nucleophile group comprises a primary amine or a primary thiol (32) as in any of 28-31 wherein the first precursor and the second precursor are water soluble (33) as in any of 28-32 wherein at least one of the first precursor and the second precursor comprises a synthetic polymer (34) as in any of 28-33 wherein the first precursor comprises a polymer chosen from the group consisting of polyethylene glycol, polyacrylic acid, polyvinylpyrrolidone, and block copolymers thereof (35) as in any of 1-34 comprising the organogel, comprising preparing the organogel as a structure chosen from the group consisting of a rod, a sheet, a particle, a sphere, and a collection of at least one of the same (36) as in any of 1-35 comprising, or further comprising a therapeutic agent, wherein the agent comprises a fluoroquinolone, moxifloxacin, travoprost, dexamethasone, an antibiotic, or a vestibulotoxin (37) as in 36 with the organogel further comprising a permeation enhancer (38) as in any of 1-8 wherein the organogel is physically crosslinked by formation of domains, the process further comprising forming the organogel from a precursor in an organic solvent, with the precursor being a block copolymer that comprises a first block and a second block (39) as in 38 comprising heating a mixture of the precursor and the organic solvent and allowing the solution to cool, thereby precipitating at least the first block of the copolymeric precursor, with said domains comprising at least the first block (40) as in 38 or 39 comprising mixing the precursor in a first organic solvent that dissolves the copolymeric precursor, with all of the blocks of the copolymeric precursor being soluble in the first organic solvent, and adding a second organic solvent that is miscible with the first organic solvent, with the first block of the copolymeric precursor being insoluble in the second organic solvent, with the second solvent being effective to form the domains, with the domains comprising the first block of the copolymer (41) as in any of 38-40 wherein the copolymeric precursor comprises a block chosen from the group consisting of polyethylene glycol (42) as in any of 38-41 wherein the copolymeric precursor further comprises a second block chosen from the group consisting of polylactic acid, polyglycolic acid, polytrimethylene carbonate, polydioxanone, polyakyl, polybutylene terephthalate, and polylysine (43) as in any of 1-37 wherein the organogel is free of hydrophobic materials; alternatively being free of hydrophobic polymers, or being free of all hydrophobic materials with the exception of solvents (which may be somewhat hydrophobic) (44) as in any of 1-43 comprising preparing a powder of the biologic according to a method that avoids denaturation of the biologic, and, once the powder has been prepared, preventing exposure of the powder to water (45) as in any of 1-44 wherein the biologic is therapeutic protein having a secondary and/or tertiary structure (46) as in any of 1-45 comprising a xerogel, wherein the xerogel is a hydrogel after being exposed to water (47) as in any of 1-46 wherein the hydrogel, or a hydrogel made from the gel/organogel/xerogel is biodegradable (48) as in any of 1-47 comprising the xerogel, wherein a cumulative amount of release of the agent reaches 90% w/w of the agent at a time between about 1 month and about 6 months after placement of the hydrogel and particles in a saline solution (49) a biomaterial as in any of 1-48 (50) a biomaterial as in any of 1-49 wherein the xerogel comprises covalently crosslinked hydrophilic polymers (51) a biomaterial as in any of 1-50 wherein the water soluble biologic is a protein having a secondary and/or tertiary structure (52) a biomaterial as in any of 1-51 wherein the water soluble biologic remains substantially in the solid phase, when the hydrogel is formed, and slowly dissolves over a period of time when the hydrogel is exposed to physiological solution in vivo in a mammal (53) a biomaterial as in any of 1-52 comprising the organogel, wherein the organogel comprises covalently crosslinked hydrophilic polymers (54) the biomaterial of 53 wherein the polymers comprise a member chosen from the group consisting of polyethylene oxide, polyvinyl pyrrolidinone, hyaluronic acid, polyhydroxyethlymethacrylate, and block copolymers thereof (54) as in any of 1-53 with the material being a structure chosen from the group consisting of a rod, a sheet, a particle, a sphere, and a collection thereof (55) any of 1-54 comprising the xerogel, or a process of providing the xerogel as, a collection of particles, e.g., by a method chosen from the group consisting of (a) making the organogel and breaking it up to form particles for the collection, (b) making the xerogel and breaking up the xerogel to form particles for the collection, and (c) making the organogel as a plurality of particles for the collection, said particles being stripped of the organic solvent(s) to make the xerogel (56) a process as in 55 comprising making a plurality of the collections of particles, with the collections having different rates of degradation in vivo, and mixing collections to make a biomaterial having a degradation performance as desired.

These embodiments 1-56 may further be prepared as a kit with the polymers, biologic or protein, and an applicator, with the kit being in a sterile container. These embodiments 1-56 may be further practiced by placing the material, or a material made by one of the processes, in contact with a tissue of a patient. Examples of the tissues are an intraperitoneal space, a muscle, a dermis, an epidermis, a natural lumen or void, an abdominal cavity, a prostate, a rectum, a location between a prostate and a rectum, a breast, a tissue between a radiation target and healthy tissue, and a vasculature.

EXAMPLES

Example 1

Preparation of Organogels and Xerogels Containing Protein Particles

Polyethylene Glycol (PEG) Compounds

PEG compounds were obtained with the following structures:

TABLE 1

PEG Esters

| PEG Molecular weight (Da) | Number of PEG arms | End group moiety | Reactive end group | Designation |
|---|---|---|---|---|
| 15000 | 8 | Succinic acid | N-hydroxysuccinimide | 8a15KSS |
| 20000 | 4 | Glutaric acid | N-hydroxysuccinimide | 4a20KSG |
| 15000 | 8 | Glutaric acid | N-hydroxysuccinimide | 8a15KSG |
| 20000 | 4 | Adipic acid | N-hydroxysuccinimide | 4a20KSAP |
| 20000 | 4 | Glutaric amide | N-hydroxysuccinimide | 4a20KSGA |
| 20000 | 8 | None | Free amine | 8a20KA or 8a20KNH2 |

Preparation of PEG Solutions

PEG powders were weighed out and put in a 10 ml graduated cylinder as in the following Tables:

TABLE 2

Preparation of PEG Ester solutions in Methylene Chloride

| Example | PEG Ester | (g) |
|---|---|---|
| 1A-1 | 8a15kSS | 0.86 |
| 1B-1 | 4a20kSG | 1.33 |
| 1C-1 | 8a15kSG | 0.86 |
| 1D-1 | 4a20kSAP | 1.33 |
| 1E-1 | 4a20kSGA | 1.33 |

TABLE 3

Preparation of PEG Amine solutions in Methylene Chloride

| Example | PEG Amine | (g) |
|---|---|---|
| 1A-2 | 8a20KNH2 | 1.14 |
| 1B-2 | 8a20KNH2 | 0.67 |
| 1C-2 | 8a20KNH2 | 1.14 |
| 1D-2 | 8a20KNH2 | 0.67 |
| 1E-2 | 8a20KNH2 | 0.67 |

Methylene chloride was added to the 10 mL mark once the PEG was dissolved.

Preparation of Ground Ovalbumin

In a nitrogen-filled glove bag, ovalbumin (Worthington Biochemical Corporation; LS003048) was ground using a mortar and pestle and sieved to less than 20 μm particles through a stainless steel sieve.

Preparation of Ovalbumin Organogels

Ground ovalbumin was weighed in a polyethylene female LUER-LOK syringe. PEG Amine solution was mixed with the ovalbumin to form a suspension. PEG Ester solution was put in a male polyethylene luer Lock syringe. The syringes were mated and solutions were mixed syringe-to-syringe for 10 seconds and allowed to stand in the male syringe for 10 minutes, during which time was formed a gel containing the protein. The syringe was cut open and the gel-protein cylinder was removed. The gels were place under vacuum overnight to dry. The following Table summarizes the samples prepared in this manner.

TABLE 4

Albumin Organogel Preparation

| | PEG Ester | | PEG Amine | | Protein |
|---|---|---|---|---|---|
| Example | Example | Amount (μL) | Example | Amount (μL) | ovalbumin (mg) |
| 1A-3 | 1A-1 | 500 | 1A-2 | 500 | 103.5 |
| 1B-3 | 1B-1 | 500 | 1B-2 | 500 | 106 |
| 1C-3 | 1C-1 | 500 | 1C-2 | 500 | 105.1 |
| 1D-3 | 1D-1 | 500 | 1D-2 | 500 | 102.4 |
| 1E-3 | 1E-1 | 500 | 1E-2 | 500 | 100.2 |

Preparation of Ovalbumin-PEG Xerogels

The syringe containing the ovalbumin organogel was cut open and the gel-protein cylinder was removed. The gels were placed under vacuum overnight to dry. Dried xerogels were stored under nitrogen headspace at 5° C.

Preparation of Ground Rabbit IgG

In a nitrogen-filled glove bag, rabbit IgG (IgG from Rabbit serum; Sigma; >95%) was hand ground using a mortar and pestle and sieved to less than 20 μm through a stainless steel sieve.

Preparation of Rabbit IgG Organogels

Ground rabbit IgG was weighed in a polyethylene female luer lock syringe. PEG Amine solution was mixed with the ovalbumin to form suspension. PEG Ester solution was put in male polyethylene LUER-LOK syringe. The syringes were mated and solutions were mixed syringe-to-syringe for 10 seconds and allowed to stand in the male syringe for 10 minutes to form the gel containing protein. The syringe was cut open and the gel-protein cylinder was removed. The gels were place under vacuum overnight to dry. The table below summarizes the samples prepared in this manner. The following Table summarizes the samples prepared in this manner.

TABLE 5

Rabbit IgG Organogel preparation

| | PEG Ester | | PEG Amine | | Protein |
|---|---|---|---|---|---|
| Example | Example | Amount (μL) | Example | Amount (μL) | Rabbit IgG (mg) |
| 1A-4 | 1A-1 | 100 | 1A-2 | 100 | 9.47 |
| 1B-4 | 1B-1 | 100 | 1B-2 | 100 | 9.52 |
| 1C-4 | 1C-1 | 100 | 1C-2 | 100 | 9.78 |
| 1D-4 | 1D-1 | 100 | 1D-2 | 100 | 10.29 |
| 1E-4 | 1E-1 | 100 | 1E-2 | 100 | 10.4 |

Preparation of Rabbit IgG-PEG Xerogels

The syringe containing the rabbit IgG organogel was cut open and the gel-protein cylinder was removed. The gels were place under vacuum overnight to dry. Dried xerogels were stored under nitrogen headspace at 5° C.

Example 2

In Vitro Release of Proteins from Hydrogels

Stability of Protein in Buffer Solutions

Ovalbumin (Worthington Biochemical Corporation; LS003048) and rabbit IgG (IgG from Rabbit serum; Sigma; >95%) were dissolved in TRIS Buffer at 0.065 mg/ml. Initial samples were taken for baseline and at various time points to determine protein stability in the buffer. Samples were analyzed for protein content by HPLC and ELISA. The results are summarized in the tables below.

TABLE 6

HPLC Protein Stability Study
(50 mL Tris Buffer, pH 8.5, shaking at 50 rpm)

| Elapsed Time (hr) | Ovalbumin recovered | IgG recovered |
|---|---|---|
| 0.00 | 100.0% | 100.0% |
| 2.00 | 98.3% | 97.1% |
| 6.00 | 97.2% | 99.5% |
| 24.00 | 95.5% | 97.7% |
| 48.00 | 95.0% | 98.3% |
| 96.00 | 94.1% | 93.3% |

TABLE 7

ELISA Protein Stability Study
(50 mL Tris Buffer, pH 8.5, shaking at 50 rpm, 37 C.)

| Elapsed Time (hr) | Ovalbumin recovered | IgG recovered |
|---|---|---|
| 5 min | 97.7% | 109.5% |
| 2 hour | 99.5% | 87.1% |
| 6 hour | 98.4% | 85.5% |
| 24 hour | 91.3% | 76.0% |
| 48 hour | 99.9% | 78.8% |
| 96 hour | 70.1% | 83.8% |

The results show the proteins are sufficiently stable for use with accelerated in vitro protein release testing.

In Vitro Protein Sustained Release Study

Samples of xerogels from Example 1 were cut, weighed and added to 50 ml TRIS buffer in a 50 mL centrifuge tube. Stainless steel dissolution cages were used to hold the sample in the bottom half of the centrifuge tube. The tubes were submerged in a shaking water bath at 37° C. and 50 RPM.

TABLE 8

Accelerated and Real-Time In Vitro Protein Release Study

| Example | Xerogel from Example | Protein | protein in sample (mg) | Buffer pH | Buffer Temperature (° C.) |
|---|---|---|---|---|---|
| 2A | 1A-3 | ovalbumin | 24.46 | 8.5 | 37 |
| 2B | 1B-3 | ovalbumin | 23.77 | 8.5 | 37 |
| 2C | 1C-3 | ovalbumin | 23.37 | 8.5 | 37 |
| 2D | 1D-3 | ovalbumin | 22.82 | 8.5 | 37 |
| 2E | 1E-3 | ovalbumin | 20.22 | 8.5 | 37 |
| 2F | 1A-3 | ovalbumin | 25.12 | 7.4 | 37 |
| 2G | 1A-4 | IgG | 5.11 | 8.5 | 37 |
| 2H | 1B-4 | IgG | 8.84 | 8.5 | 37 |
| 2I | 1C-4 | IgG | 9.95 | 8.5 | 37 |
| 2J | 1D-4 | IgG | 10.8 | 8.5 | 37 |
| 2K | 1E-4 | IgG | 10.66 | 8.5 | 37 |

Buffer medium samples were taken at 2 hrs, 4 hrs, 8 hours and then every 8 hours after that until the gel degraded. Buffer medium was fully exchanged at every time point. The samples collected were analyzed by HPLC and ELISA. The results are shown graphically below in FIGS. 2-5.

Drug Release Profile Customization

Combinations of the various vehicles may be used to customize a release rate for a therapeutic agent. The release rates for various particles were combined and a composite total release rate was calculated, as depicted in FIGS. 6 and 7. FIG. 6 depicts a substantially zero-order release kinetics from about 10 to about 60 hours. FIG. 7 depicts a finely tuned system. There is a first release that provides an initial burst for the first 24 hours, followed by additional zero order release from about 24 to about 100 hours. The zero-order release is sustained through the final dissolution of the materials.

Example 3

Formation of a Crosslinked Gel from a Melt of Precursors 0.86 g of an 8-armed branched PEG of about 15,000 Daltons terminated with SS (8a15KSS) was melted at 50° C. 1.14 g of an 8-armed branched PEG of about 20,000 Daltons terminated with primary amines (8a20 KNH2) was weighed with 0.5 g of bovine serum albumin (BSA) powder in a 10 ml syringe and then soaked in a water bath at 60° C. to melt 8a20 KNH2. A drop of the 8a15KSS melt was placed on a 50° C. hot plate surface next to a drop of 8a20 KNH2melt/BSA. Drops were mixed quickly to gel within less than 2 seconds. Gels formed contain BSA particles in the solid form as observed by microscopy.

Formed gels were transferred to scintillation vials filled with Tris-buffered physiological saline (TBS) pH8.5 buffer to rapidly hydrolyze the polymer and release the BSA.

After gel degradation, the resulting TBS release media was noted to be clear indicating the solubility of BSA in TBS and did not show processing effects on the protein solubility in terms of aggregation or denaturation.

Patents, patent applications, patent publications, and references set forth herein are hereby incorporated herein by reference for all purposes; in the case of conflict, the instant specification controls.

The invention claimed is:

1. A biomaterial for controlled release of a therapeutic water soluble biologic comprising
    a pharmaceutically acceptable xerogel and
    solid particles having a diameter from 1 μm to 30 μm and consisting essentially of the therapeutic water soluble biologic and a water soluble sugar stabilizing the therapeutic water soluble biologic,
    with the particles being dispersed in the xerogel, with the xerogel being a hydrogel when exposed to water.

2. The biomaterial of claim 1 wherein the xerogel comprises covalently crosslinked hydrophilic polymers.

3. The biomaterial of claim 1 wherein the therapeutic water soluble biologic is a protein having a secondary and/or tertiary structure.

4. The biomaterial of claim 1 wherein the therapeutic water soluble biologic remains substantially in the solid phase when the hydrogel is formed and the therapeutic water soluble biologic slowly dissolves over a period of time when the hydrogel is exposed to physiological solution in vivo in a mammal.

5. The biomaterial of claim 1 wherein the xerogel consists essentially of covalently crosslinked hydrophilic polymers.

6. The biomaterial of claim 1 wherein the xerogel, when hydrated in water, is biodegradable by spontaneous hydrolysis of hydrolytically degradable linkages chosen from the group consisting of esters, carbonates, anhydrides and orthocarbonates.

7. The biomaterial of claim 1 wherein the xerogel is a chemical reaction product of a first precursor comprising a first functional group and a second precursor comprising a second functional group, with the first functional group and the second functional group reacted to form covalent bonds.

8. The biomaterial of claim 1 wherein the therapeutic water soluble biologic is a protein or is an oligopeptide having a molecular weight of no more than 5000 Daltons as measured by number weight average.

9. The biomaterial of claim 1 wherein the xerogel is free of hydrophobic materials.

10. A punctal plug comprising the biomaterial of claim 1.

11. A method of controlled release of a therapeutic water soluble biologic comprising placing the biomaterial of claim 1 in contact with a tissue of a patient.

12. The method of claim 11, wherein the tissue comprises a structure selected from the group consisting of an intraperitoneal space, a muscle, a dermis, an epidermis, a natural lumen or void, an abdominal cavity, a prostate, a rectum, and a vasculature.

13. The method of claim 11 wherein the tissue is an eye.

14. The method of claim 11 wherein the tissue is an anterior chamber of an eye, a posterior chamber of an eye, or a vitreous of an eye.

15. The method of claim 11 wherein the tissue is a punctum of an eye.

16. The method of claim 11 wherein the water soluble sugar comprises sucrose or trehalose.

* * * * *

UNITED STATES PATENT AND TRADEMARK OFFICE
CERTIFICATE OF CORRECTION

Page 1 of 1

PATENT NO. : 10,905,765 B2
APPLICATION NO. : 14/926707
DATED : February 2, 2021
INVENTOR(S) : Jarrett et al.

It is certified that error appears in the above-identified patent and that said Letters Patent is hereby corrected as shown below:

On the Title Page

Column 2, item (56), Line 1, delete "al." and insert -- al., --, therefor.

Page 3, Column 2, item (56), Line 3, delete "Microsphers" and insert -- Microspheres --, therefor.

Page 3, Column 2, item (56), Line 4, delete "Surger"," and insert -- Surgery", --, therefor.

Page 3, Column 2, item (56), Line 4, delete "Opthalmol" and insert -- Ophthalmol. --, therefor.

Page 3, Column 2, item (56), Line 10, delete "5&" and insert -- 5 & --, therefor.

Page 3, Column 2, item (56), Line 14, delete "al." and insert -- al., --, therefor.

Page 3, Column 2, item (56), Line 18, delete "al." and insert -- al., --, therefor.

Page 3, Column 2, item (56), Line 24, delete "Neocasculat" and insert -- Neovascular --, therefor.

Page 3, Column 2, item (56), Line 25, delete "http://www-revophth.com/content/" and insert -- http://www.revophth.com/content/ --, therefor.

Page 3, Column 2, item (56), Line 28, delete "al." and insert -- al., --, therefor.

In the Claims

Column 42, Claim 1, Line 58, delete "comprising" and insert -- comprising: --, therefor.

Column 42, Claim 1, Line 59, delete "xerogel and" and insert -- xerogel; and --, therefor.

Column 44, Claim 12, Line 9, delete "claim 11," and insert -- claim 11 --, therefor.

Signed and Sealed this
First Day of June, 2021

Drew Hirshfeld
*Performing the Functions and Duties of the*
*Under Secretary of Commerce for Intellectual Property and*
*Director of the United States Patent and Trademark Office*